United States Patent [19]
Fujiwara et al.

[11] Patent Number: 5,948,784
[45] Date of Patent: Sep. 7, 1999

[54] QUINAZOLINE DERIVATIVES

[75] Inventors: Shigeki Fujiwara, Mishima; Yuko Okamura, Numazu; Haruki Takai, Shizuoka; Hiromi Nonaka, Shizuoka; Takahiro Moriyama, Shizuoka; Kozo Yao, Shizuoka; Akira Karasawa, Shizuoka, all of Japan

[73] Assignee: Kyowa Hakko Kogyo Co., Ltd., Tokyo, Japan

[21] Appl. No.: 09/089,255

[22] Filed: Jun. 3, 1998

Related U.S. Application Data

[63] Continuation-in-part of application No. 08/634,417, filed as application No. PCT/JP95/01694, Aug. 25, 1995, abandoned.

[30] Foreign Application Priority Data

Aug. 26, 1994 [JP] Japan ................................ 6-202018

[51] Int. Cl.⁶ ...................... C07D 401/14; A61K 31/505
[52] U.S. Cl. ......................... 514/260; 514/212; 514/218; 514/228.2; 514/232.5; 544/284; 544/58.5; 544/80; 544/119; 540/575; 540/600
[58] Field of Search .................... 514/260, 257, 514/212, 232.5; 544/284, 250, 247, 58.5; 540/575

[56] References Cited

U.S. PATENT DOCUMENTS

| 5,296,487 | 3/1994 | Shimazaki et al. ................... 514/259 |
| 5,605,900 | 2/1997 | Fujiwara et al. ..................... 514/248 |
| 5,624,926 | 4/1997 | Fujiwara et al. ..................... 514/248 |

FOREIGN PATENT DOCUMENTS

| 0638567 | 2/1995 | European Pat. Off. . |
| 2347376 | 4/1974 | Germany . |
| 49-69684 | 7/1974 | Japan . |
| 1438405 | 6/1976 | United Kingdom . |

OTHER PUBLICATIONS

Chem. Pharm. Bull, vol. 38, No. 6 (1990) 1591–1595.
Gruber et al., Circulation, vol. 80, no. 5 (1989) 1400–11.
Young et al., Am. J. Physiol. (1991) H1570–77.
Van Belle et al., J. Cardio. Pharm., vol. 20, No. 2 (1992) 173–78.
Takai et al., Chem. Pharm. Bull., vol. 34, No. 5 (1986) 1907–16.
Hess et al., J. Med. Chem., vol. 11 91968) 130–37.
Nomoto et al., Chem. Pharm. Bull. vol. 38, No. 11 (1990) 3014–19.

*Primary Examiner*—John M. Ford
*Attorney, Agent, or Firm*—Fitzpatrick, Cella, Harper & Scinto

[57] ABSTRACT

Disclosed are quinazoline derivatives represented by formula (I):

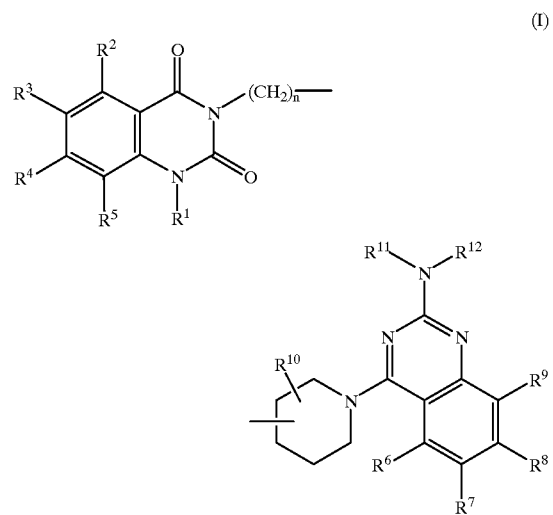

wherein $R^1$ represents hydrogen, lower alkyl, alkenyl, or aralkyl; $R^2$, $R^3$, $R^4$, and $R^5$ represent hydrogen, lower alkyl, lower alkoxy, lower alkanoyl, or the like; $R^6$, $R^7$, $R^8$, and $R^9$ represent hydrogen, lower alkyl, lower alkoxy, aralkyloxy, or the like, or any adjoining two of them are combined to form methylenedioxy or the like; $R^{10}$ represents hydrogen, lower alkyl, or the like; $R^{11}$ and $R^{12}$ represent hydrogen, lower alkyl, cycloalkyl, phenyl, or aralkyl, or $R^{11}$ and $R^{12}$ are combined together with N to form a heterocyclic group; and n represents 0, 1 or 2, and pharmaceutically acceptable salts thereof. These compounds have adenosine uptake inhibitory activity and are useful for the protection of myocardium and for the prevention or treatment of renal diseases such as nephritis and diabetic nephropathy.

10 Claims, No Drawings

QUINAZOLINE DERIVATIVES

This is a continuation-in-part of U.S. patent application Ser. No. 08/634,417 filed on Apr. 18, 1996 (now abandoned) which is a 371 of PCT/JP95/01694 filed Aug. 25, 1995.

BACKGROUND OF THE INVENTION

The present invention relates to quinazoline derivatives and pharmaceutically acceptable salts thereof which have adenosine uptake inhibitory activity and are useful for the protection of myocardium and for the prevention or treatment of renal diseases such as nephritis and diabetic nephropathy.

With respect to 1,2,3,4-tetrahydro-2,4-dioxoquinazoline derivatives having a 1-(6,7-dimethoxy-4-quinazolinyl)-4-piperidinyl group at the 3-position, those having a hydrogen atom, a chlorine atom or a nitro group at the 6-position are described in Chem. Pharm. Bull., 38, 1591–1595 (1990). In WO 94/19342, 1,2,3,4-tetrahydro-2,4-dioxoquinazoline derivatives having other substituents are described.

On the other hand, it is known that a compound having adenosine uptake inhibitory activity exhibits myocardium protecting activity [Circul., 80, 1400–1411 (1989); Am. J. Physiol., H1570–1577 (1991); J. Cardiovasc. Pharmacol., 20, 173–178 (1992)]. It is also known that anti-platelet agents, corticosteroids, immunosuppressive agents, anticoagulants, etc. are useful as therapeutic agents for nephritis [Medical Practice, 9, 376–386 (1992); Modern Physician, 15, 1273–1275 (1995)]. Further, angiotensin converting enzyme inhibitors are known to be effective against diabetic nephropathy [Sogo Rinsho, 41, 2784–2789 (1992); Jin To Toseki (Kidney and Dialysis), 37, 735–739 (1994)].

SUMMARY OF THE INVENTION

The present invention relates to quinazoline derivatives represented by formula (I):

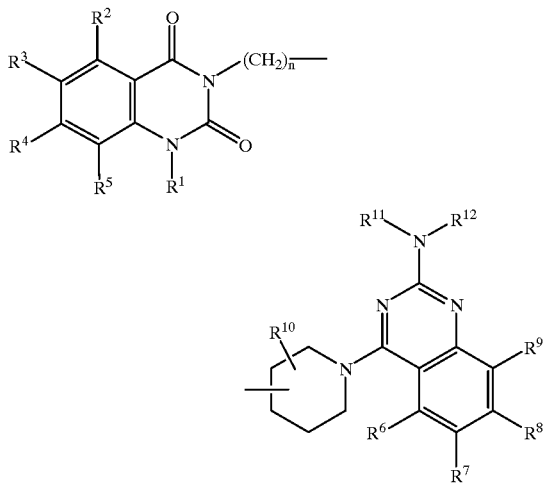

wherein $R^1$ represents hydrogen, substituted or unsubstituted lower alkyl, alkenyl, or substituted or unsubstituted aralkyl; $R^2$, $R^3$, $R^4$, and $R^5$ independently represent hydrogen, halogen, amino, mono- or di(lower alkyl)amino, lower alkanoylamino, nitro, cyano, substituted or unsubstituted lower alkyl, hydroxy, lower alkoxy, lower alkylthio, carboxy, lower alkoxycarbonyl, lower alkanoyl, aralkyloxy, or lower alkanoyloxy; $R^6$, $R^7$, $R^8$, and $R^9$ independently represent hydrogen, lower alkyl, hydroxy, substituted or unsubstituted lower alkoxy, or aralkyloxy, lower alkanoyloxy, or any adjoining two of them are combined to form methylenedioxy or ethylenedioxy; $R^{10}$ represents hydrogen, lower alkyl, or halogen; $R^{11}$ and $R^{12}$ independently represent hydrogen, substituted or unsubstituted lower alkyl, cycloalkyl, substituted or unsubstituted phenyl, or substituted or unsubstituted aralkyl, or $R^{11}$ and $R^{12}$ are combined together with N to form a substituted or unsubstituted heterocyclic group; and n represents 0, 1 or 2, and pharmaceutically acceptable salts thereof.

DETAILED DESCRIPTION OF THE INVENTION

The compounds represented by formula (I) are hereinafter referred to as Compounds (I). The same applies to the compounds of other formula numbers.

In the definitions of the groups in formula (I), the lower alkyl and the lower alkyl moiety of the mono- or di(lower alkyl)amino, the lower alkanoylamino, the lower alkoxy, the lower alkylthio, the lower alkoxycarbonyl, the lower alkanoyl and the lower alkanoyloxy mean a straight-chain or branched alkyl group having 1 to 8 carbon atoms, such as methyl, ethyl, propyl, isopropyl, butyl, isobutyl, sec-butyl, tert-butyl, pentyl, isopentyl, hexyl, heptyl, and octyl. The alkenyl means a straight-chain or branched alkenyl group having 2 to 6 carbon atoms, such as vinyl, allyl, methacryl, crotyl, 3-butenyl, 2-pentenyl, 4-pentenyl, 2-hexenyl, and 5-hexenyl. The cycloalkyl means a cycloalkyl group having 3 to 8 carbon atoms, such as cyclopropyl, cyclobutyl, cyclopentyl, cyclohexyl, cycloheptyl, and cyclooctyl. The aralkyl and the aralkyl moiety of the aralkyloxy mean an aralkyl group having 7 to 13 carbon atoms, such as benzyl, phenethyl, benzhydryl, and naphthylmethyl. The heterocyclic group includes pyrrolidinyl, piperidino, piperazinyl, morpholino, thiomorpholino, homopiperazinyl, and homopiperidino. The halogen includes fluorine, chlorine, bromine, and iodine.

The substituted lower alkyl and the substituted lower alkoxy each has 1 to 3 independently selected substituents. Examples of the substituents are halogen, nitro, cyano, hydroxy, lower alkoxy, carboxy, lower alkoxycarbonyl, lower alkanoyl, cycloalkyl, amino, mono- or di(lower alkyl)amino, phthalimide, $CONR^{13}R^{14}$ (wherein $R^{13}$ and $R^{14}$ are independently represent hydrogen, lower alkyl, or $R^{13}$ and $R^{14}$ are combined together with N to form heterocyclic group). The substituted phenyl and the substituted aralkyl each has 1 to 3 independently selected substituents on the benzene ring thereof. Examples of the substituents are halogen, lower alkyl, nitro, cyano, amino, mono- or di(lower alkyl)amino, hydroxy, lower alkoxy, carboxy, lower alkoxycarbonyl, lower alkanoyl, methylenedioxy, and trifluoromethyl. The substituted heterocyclic group has 1 to 3 independently selected substituents. Examples of the substituents are halogen, lower alkyl, amino, mono- or di(lower alkyl)amino, hydroxy, lower alkoxy, carboxy, lower alkoxycarbonyl, lower alkanoyl, trifluoromethyl, phenyl, and aralkyl.

In the definitions of the substituents, the halogen, the lower alkoxy, the lower alkoxycarbonyl, the lower alkanoyl, the cycloalkyl, the mono- or di(lower alkyl)amino, the lower alkyl, aralkyl, and heterocyclic group have the same meanings as defined above.

The pharmaceutically acceptable salts of Compounds (I) include pharmaceutically acceptable acid addition salts, metal salts, ammonium salts, organic amine addition salts, and amino acid addition salts.

Examples of the pharmaceutically acceptable acid addition salts of Compounds (I) are inorganic acid addition salts such as hydrochloride, sulfate, and phosphate, and organic acid addition salts such as acetate, maleate, fumarate, tartrate, citrate, and methanesulfonate. Examples of the pharmaceutically acceptable metal salts are alkali metal salts such as sodium salt and potassium salt, alkaline earth metal salts such as magnesium salt and calcium salt, aluminum salt, and zinc salt. Examples of the pharmaceutically acceptable ammonium salts are ammonium salt and tetramethylammonium salt. Examples of the pharmaceutically acceptable organic amine addition salts are salts with morpholine and piperidine. Examples of the pharmaceutically acceptable amino acid addition salts are salts with lysine, glycine, and phenylalanine.

The processes for preparing Compounds (I) and the intermediates are described below.

Process 1: Process for preparing Compound (I)

Compound (I) can be prepared according to the following reaction step:

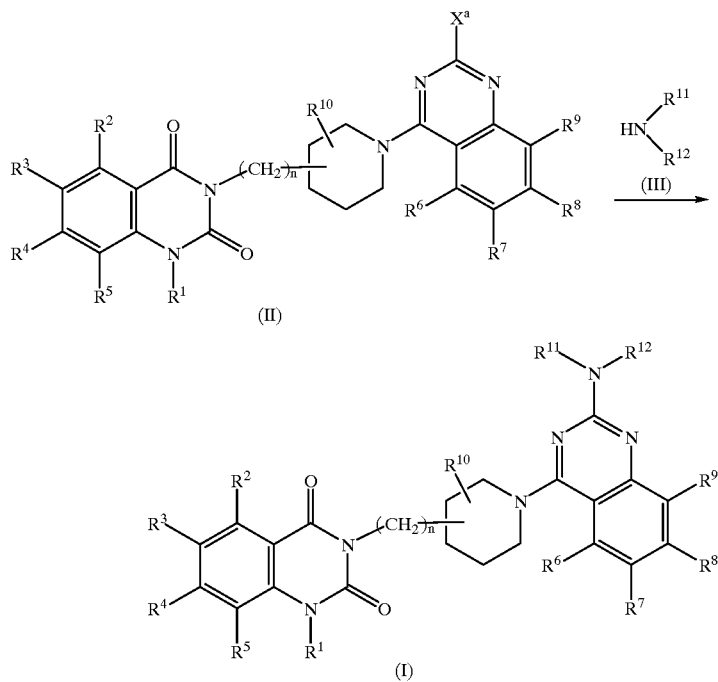

(In the formulae, $X^a$ represents chlorine, bromine, iodine, methanesulfonyloxy, benzenesulfonyloxy, or toluenesulfonyloxy; and $R^1$, $R^2$, $R^3$, $R^4$, $R^5$, $R^6$, $R^7$, $R^8$, $R^9$, $R^{10}$, $R^{11}$, $R^{12}$, and n have the same meanings as defined above.)

(Step 1)

Compound (I) can be obtained by reaction of Compound (II) with Compound (III) in an appropriate solvent, such as a lower alcohol, e.g., methanol, ethanol, or isopropanol, a cyclic ether, e.g., tetrahydrofuran (THF) or 1,4-dioxane, dimethylformamide (DMF), dimethylacetamide (DMA), N-methylpyrrolidinone, dimethyl sulfoxide (DMSO), or a mixture thereof, at a temperature between room temperature and the boiling point of the solvent used for 10 minutes to 48 hours. If necessary, the reaction is carried out in the presence of a base, such as a tertiary amine, e.g., triethylamine or pyridine, or an alkali metal carbonate, e.g., sodium carbonate or potassium carbonate. Compound (III) is used in an amount of 1 equivalent based on Compound (II) to the amount of solvent. Further, potassium iodide, sodium iodide, or the like may be added during the reaction as may be appropriate. By the use of a primary amine as Compound (III) and DMF as the solvent, Compound (I) wherein $R^{11}$ and $R^{12}$ are both methyl can be obtained.

Process 2: Process for preparing Compound (II-a), i.e., Compound (II) wherein $R^1$ is hydrogen Compound (II-a) can be prepared according to the following reaction steps:

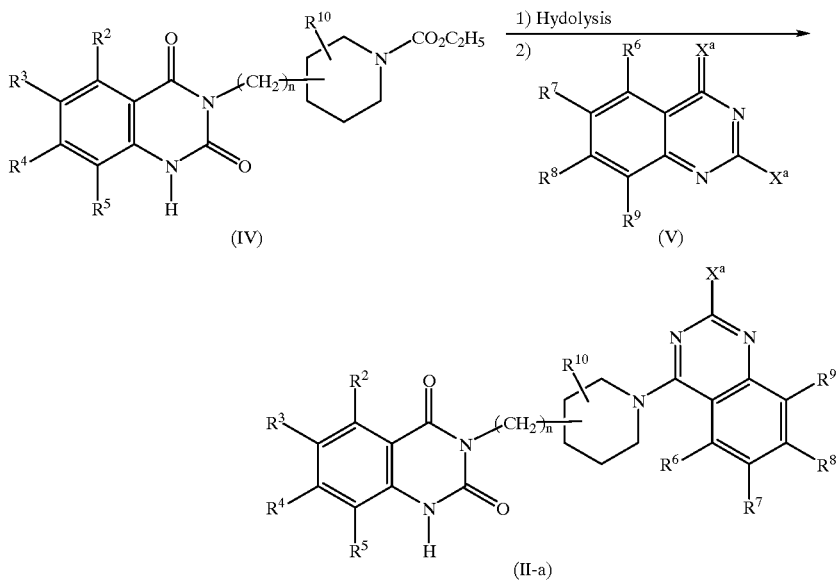

(In the formulae, $X^a$, $R^2$, $R^3$, $R^4$, $R^5$, $R^6$, $R^7$, $R^8$, $R^9$, $R^{10}$, and n have the same meanings as defined above.)

The starting Compound (IV) can be obtained according to the method described in Chem. Pharm. Bull., 34, 1907–1916 (1986).

(Step 2)

The ethoxycarbonyl group of Compound (IV) is hydrolyzed in the presence of an acid, such as sulfuric acid, hydrochloric acid, or hydrobromic acid, in an appropriate solvent, such as water, a lower alcohol, e.g., methanol, ethanol, or isopropanol, a cyclic ether, e.g., THF or 1,4-dioxane, or a mixture thereof, at a temperature between room temperature and the boiling point of the solvent used for 10 minutes to 48 hours. Then, Compound (II-a) can be obtained by reaction of the hydrolysis product with Compound (V) [J. Med. Chem., 11, 130–139 (1968), etc.] in the presence of a base, such as a tertiary amine, e.g., triethylamine or pyridine, or an alkali metal carbonate, e.g., sodium carbonate or potassium carbonate, in an appropriate solvent, such as a lower alcohol, e.g., methanol, ethanol or isopropanol, a cyclic ether, e.g., THF or 1,4-dioxane, DMF, DMSO, or a mixture thereof, at a temperature between room temperature and the boiling point of the solvent used for 10 minutes to 48 hours according to the method described in Chem. Pharm. Bull., 38, 1591–1595 (1990).

Process 3: Process for preparing Compound (II-b), i.e., Compound (II) wherein $R^1$ is substituted or unsubstituted lower alkyl, alkenyl, or substituted or unsubstituted aralkyl Compound (II-b) can be prepared according to the following reaction step.

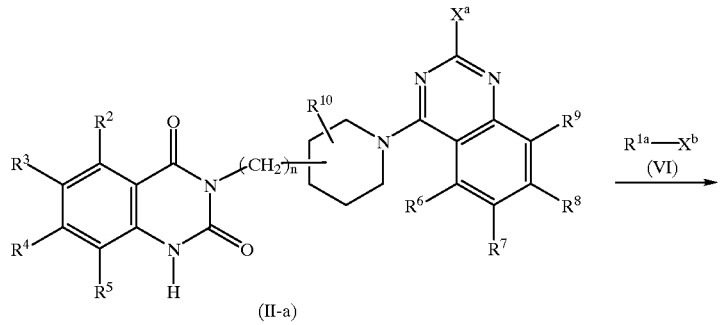

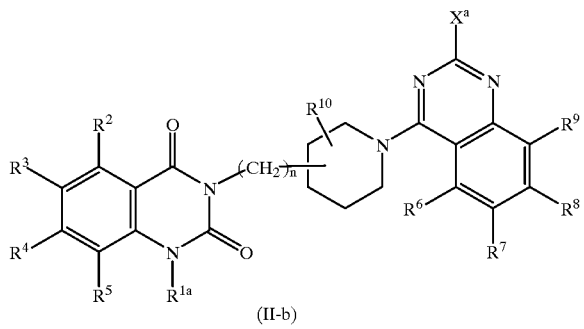

(II-b)

(In the formulae, $R^{1a}$ represents substituted or unsubstituted lower alkyl, alkenyl, or substituted or unsubstituted aralkyl; $X^b$ represents chlorine, bromine, iodine, methanesulfonyloxy, benzenesulfonyloxy, or toluenesulfonyloxy; and $X^a$, $R^2$, $R^3$, $R^4$, $R^5$, $R^6$, $R^7$, $R^8$, $R^9$, $R^{10}$, and n have the same meanings as defined above.)

(Step 3)

Compound (II-b) can be obtained by reaction of Compound (II-a) with 1 to 2 equivalents of Compound (VI) in the presence of 1 to 2 equivalents of a base, such as sodium hydride, potassium carbonate, or cesium carbonate, in an inert solvent, such as THF, DMF, acetone, or methyl ethyl ketone, at a temperature of 0° C. to the boiling point of the solvent used for 10 minutes to 24 hours.

Compound (II-b) can also be prepared according to the following reaction steps:

(In the formulae, $X^a$, $X^b$, $R^{1a}$, $R^2$, $R^3$, $R^4$, $R^5$, $R^6$, $R^7$, $R^8$, $R^9$, $R^{10}$, and n have the same meanings as defined above.)

(Step 4)

Compound (II-b) can be obtained by preparing Compound (VII) from Compound (IV) and Compound (VI) according to the same method as in Step 3 and then treating Compound (VII) in the same manner as in Step 2.

Process 4: Process for preparing Compound (I-b), i.e., Compound (I) wherein $R^1$ is substituted or unsubstituted lower alkyl, alkenyl, or substituted or unsubstituted aralkyl Compound (I-b) can also be prepared according to the following reaction step.

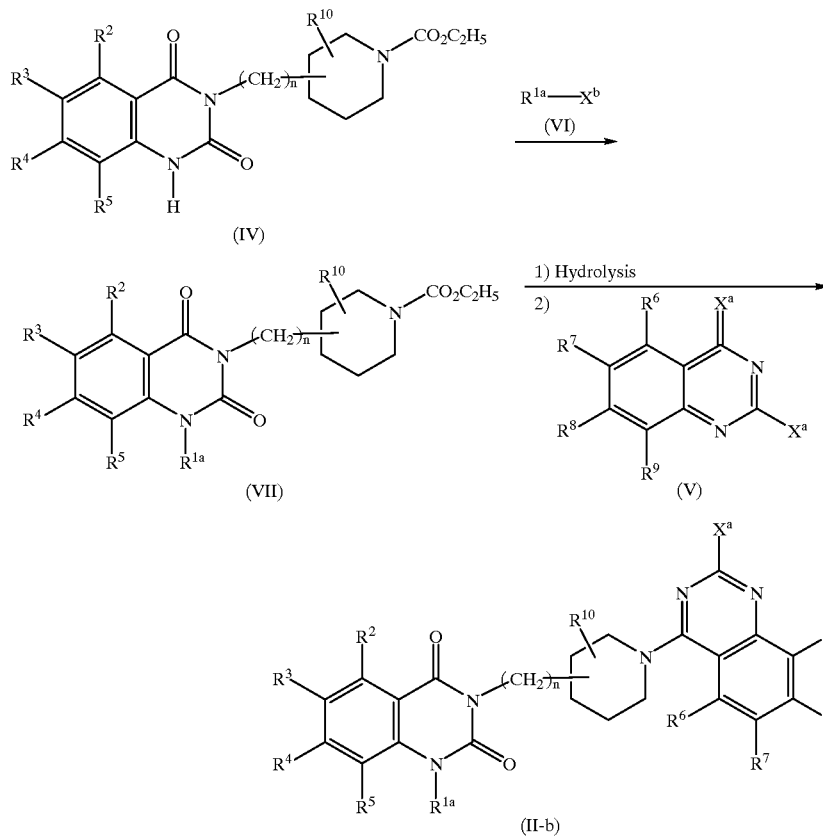

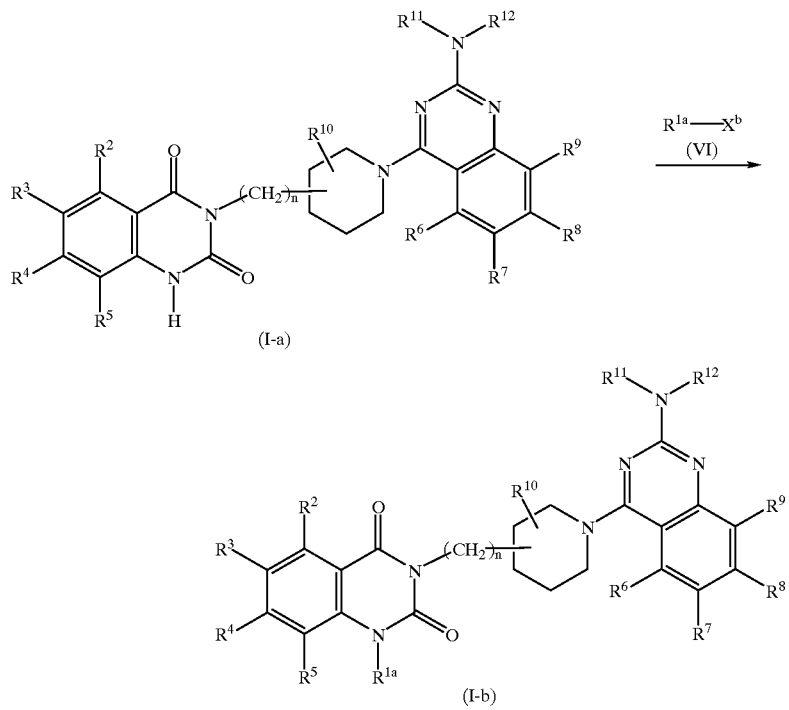
(In the formulae, $X^b$, $R^{1a}$, $R^2$, $R^3$, $R^4$, $R^5$, $R^6$, $R^7$, $R^8$, $R^9$, $R^{10}$, $R^{11}$, $R^{12}$, and n have the same meanings as defined above.)
(Step 5)
Compound (I-b) can be prepared from Compound (I-a), i.e., Compound (I) wherein $R^1$ is hydrogen, according to the same method as in Step 3.
Process 5:
Compound (I-a) can also be prepared according to the following reaction steps.
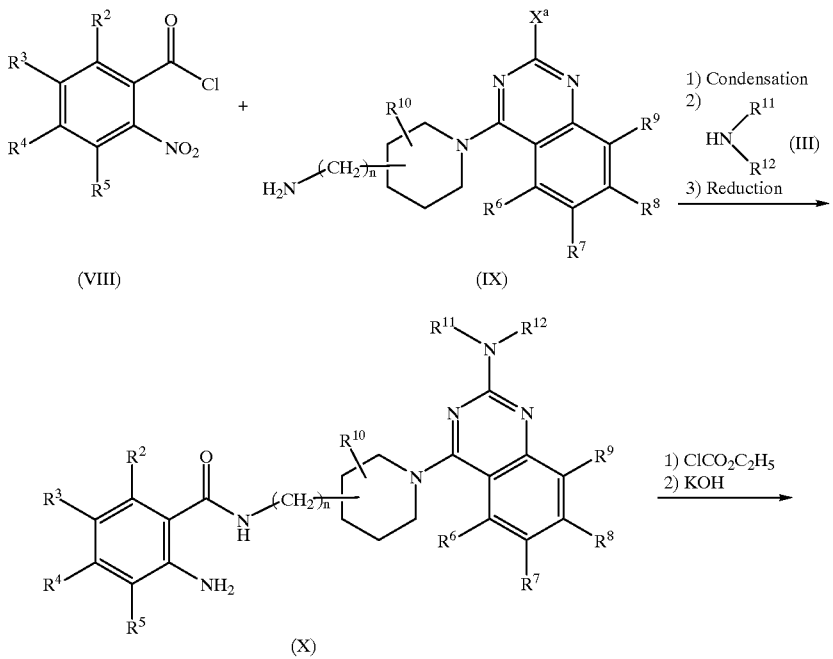

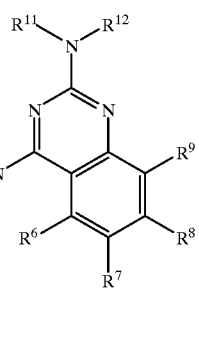

(I-a)

(In the formulae, $X^a$, $R^2$, $R^3$, $R^4$, $R^5$, $R^6$, $R^7$, $R^8$, $R^9$, $R^{10}$, $R^{11}$, and $R^{12}$ have the same meanings as defined above.)
(Step 6)

Compound (VIII) is subjected to reaction with Compound (IX) which is obtained by the method described in Chem. Pharm. Bull., 38, 3014–3019 (1990) and the literature cited therein in the presence of 1 to 10 equivalents of a base, such as triethylamine, pyridine, potassium carbonate, or cesium carbonate, in a solvent such as a halogenated hydrocarbon, e.g., chloroform or dichloromethane, an aromatic hydrocarbon, e.g., benzene or toluene, or an ether, e.g., THF, at a temperature of 0° C. to the boiling point of the solvent used for 10 minutes to 24 hours. The reaction product is subjected to reaction with Compound (III) in the same manner as in Step 1, followed by reduction of the nitro group by catalytic reduction or reduction using a metal to give Compound (X). The catalytic reduction is usually carried out in the presence of a catalyst, such as Raney nickel, palladium on carbon, or platinum oxide, in an appropriate solvent, such as methanol, ethanol, ethyl acetate, dioxane, THF, or acetic acid, at room temperature under an atmospheric pressure for 10 minutes to 48 hours. The reduction using a metal can be carried out in a zinc-acetic acid system, an iron-acetic acid system, an iron-ferric chloride-ethanol-water system, an iron-hydrochloric acid system, a tin-hydrochloric acid system, or the like, at a temperature between room temperature and the boiling point of the solvent used for 10 minutes to 48 hours.

Then, Compound (I-a) can be obtained by subjecting Compound (X) to ring closure reaction according to the method described in Chem. Pharm. Bull., 34, 1907–1916 (1986).

Compound (I) wherein at least one of $R^2$, $R^3$, $R^4$ and $R^5$ is amino, mono- or di(lower alkyl)amino, or lower alkanoylamino can also be prepared by reducing Compound (I) wherein the corresponding member(s) of $R^2$, $R^3$, $R^4$ and $R^5$ is nitro, and if necessary, alkylating or acylating the product. The reduction can be carried out in a conventional manner, for example, by catalytic reduction or reduction using a metal. The catalytic reduction is usually carried out in the presence of a catalyst, such as Raney nickel, palladium on carbon, or platinum oxide, in an appropriate solvent, such as methanol, ethanol, ethyl acetate, dioxane, THF, or acetic acid, at room temperature under an atmospheric pressure for 10 minutes to 48 hours. The reduction using a metal can be carried out in a zinc-acetic acid system, an iron-acetic acid system, an iron-ferric chloride-ethanol-water system, an iron-hydrochloric acid system, a tin-hydrochloric acid system, or the like, at a temperature between room temperature and the boiling point of the solvent used for 10 minutes to 48 hours. The alkylation or acylation of the reduction product is carried out by using a common alkylating agent (such as an alkyl halide, e.g., methyl iodide) or acylating agent (such as an acid anhydride, e.g., acetic anhydride, or an acid halide, e.g., acetyl chloride), if necessary in the presence of a base, such as pyridine, triethylamine, an alkyl metal hydroxide, or an alkyl metal carbonate, and/or a solvent, such as chloroform, dichloromethane, THF, or 1,4-dioxane, at a temperature of 0° C. to the boiling point of the solvent used for 10 minutes to 48 hours.

Compound (I) wherein at least one of $R^2$, $R^3$, $R^4$ and $R^5$ is hydroxy-substituted alkyl can also be prepared by reducing or alkylating Compound (I) wherein the corresponding member(s) of $R^2$, $R^3$, $R^4$ and $R^5$ is alkanoyl-substituted alkyl. The reduction can be carried out by using a reducing agent, such as lithium aluminum hydride or sodium boron hydride, in an appropriate solvent, such as methanol, ethanol, ethyl acetate, dioxane or THF, usually at a temperature of −78° C. to room temperature for 10 minutes to 48 hours. The alkylation is carried out by using a common organometallic reagent, such as a Grignard reagent, e.g., methylmagnesium bromide or ethylmagnesium chloride, or an organolithium reagent, e.g., methyl lithium or butyl lithium, in an appropriate solvent, such as dioxane, ether, or THF, usually at a temperature of −78° C. to room temperature for 10 minutes to 48 hours.

Compound (I) wherein at least one of $R^2$, $R^3$, $R^4$ and $R^5$ is carboxyl can also be prepared by subjecting Compound (I) wherein the corresponding member(s) of $R^2$, $R^3$, $R^4$ and $R^5$ is acetyl to haloform reaction. The haloform reaction can be carried out by using a solution of sodium hypohalogenite prepared from chlorine or bromine and an aqueous solution of sodium hydroxide, according to the method described in J. Am. Chem. Soc., 72, 1642 (1950) or the like.

Compound (I) wherein at least one of $R^6$, $R^7$, $R^8$ and $R^9$ is hydroxyl can also be prepared by subjecting Compound (I) wherein the corresponding member(s) of $R^6$, $R^7$, $R^8$ and $R^9$ is benzyloxy to the above-mentioned catalytic reduction.

Compound (I) wherein at least one of $R^2$, $R^3$, $R^4$, $R^5$, $R^6$, $R^7$, $R^8$ and $R^9$ is hydroxyl can also be prepared by dealkylating Compound (I) wherein the corresponding member(s) of $R^2$, $R^3$, $R^4$, $R^5$, $R^6$, $R^7$, $R^8$ and $R^9$ is lower alkoxy. The dealkylation can be carried out in the presence of an acid, such as hydrobromic acid or hydroiodic acid, with or without a solvent, such as water, acetic acid, or a lower alcohol, e.g., methanol or ethanol; or in the presence of at least an equivalent amount of an alkali metal salt (e.g., a sodium salt or a potassium salt) of a thiol compound, e.g., ethanethiol or thiophenol, in a solvent, such as DMF or DMSO; or in the presence of a Lewis acid, such as boron trichloride, boron tribromide, or aluminum trichloride, in a solvent, such as dichloromethane. The reaction is carried out at a temperature between room temperature and the boiling point of the solvent used and is completed in 30 minutes to 48 hours.

Compound (I) wherein at least one of $R^2$, $R^3$, $R^4$, $R^5$, $R^6$, $R^7$, $R^8$ and $R^9$ is substituted or unsubstituted lower alkoxy can also be prepared from Compound (I) wherein the corresponding member(s) of $R^2$, $R^3$, $R^4$, $R^5$, $R^6$, $R^7$, $R^8$ and $R^9$ is hydroxyl according to the same method as in Step 3.

Compound (I) wherein at least one of $R^2$, $R^3$, $R^4$ and $R^5$ is carboxyl can also be prepared by hydrolyzing Compound (I) wherein the corresponding member(s) of $R^2$, $R^3$, $R^4$ and $R^5$ is lower alkoxycarbonyl. The hydrolysis can be carried out in the presence of an acid, such as sulfuric acid, hydrochloric acid, or hydrobromic acid, or a base, such as sodium hydroxide or potassium hydroxide, in an appropriate solvent, such as water, a lower alcohol, e.g., methanol, ethanol or isopropanol, a cyclic ether, e.g., THF or 1,4-dioxane, or a mixture thereof. The reaction is carried out between room temperature and the boiling point of the solvent used and is completed in 10 minutes to 48 hours.

Compound (I) wherein at least one of $R^6$, $R^7$, $R^8$ and $R^9$ is $CONR^{13}R^{14}$-substituted alkoxy (in the formulae, $R^{13}$ and $R^{14}$ have the same meanings as defined above) can also be prepared by condensation Compound (I) wherein the corresponding member(s) of $R^6$, $R^7$, $R^8$ and $R^9$ is carboxyl-substituted lower alkoxy with $R^{13}R^{14}NH$ (in the formulae, $R^{13}$ and $R^{14}$ have the same meanings as defined above). Condensation reaction was carrired out by using conventional method in peptide synthesis.

Compound (I) wherein $R^{10}$ is hydrogen can also be prepared by subjecting Compound (I) wherein $R^{10}$ is halogen to the above-mentioned catalytic reduction.

The intermediates and desired compounds in the above-described processes can be isolated and purified by purification methods conventionally used in organic synthetic chemistry, for example, neutralization, filtration, extraction, drying, concentration, recrystallization, and various kinds of chromatography. The intermediates may be subjected to the subsequent reaction without being purified.

In the case where a salt of Compound (I) is desired and it is produced in the form of the desired salt, it can be subjected to purification as such. In the case where Compound (I) is produced in the free state and its salt is desired, Compound (I) is dissolved or suspended in a suitable organic solvent, followed by addition of an acid or a base to form a salt.

Compounds (I) and pharmaceutically acceptable salts thereof may be in the form of adducts with water or various solvents, which are also within the scope of the present invention.

Examples of Compounds (I) obtained by the above-described processes are shown in Tables 1, 2, 3 and 4.

TABLE 1(1)

| Compound | n | NR$^{11}$R$^{12}$ | R$^7$ | R$^8$ |
|---|---|---|---|---|
| 1 | 0 | (morpholino) | OCH$_3$ | OCH$_3$ |

TABLE 1(1)-continued

| Compound | n | NR$^{11}$R$^{12}$ | R$^7$ | R$^8$ |
|---|---|---|---|---|
| 2 | 0 | (4-methylpiperazinyl) | OCH$_3$ | OCH$_3$ |
| 3 | 0 | (4-CO$_2$C$_2$H$_5$-piperidinyl) | OCH$_3$ | OCH$_3$ |
| 4 | 0 | (4-CO$_2$H-piperidinyl) | OCH$_3$ | OCH$_3$ |
| 5 | 0 | N(CH$_3$)$_2$ | OCH$_3$ | OCH$_3$ |
| 6 | 0 | N(CH$_2$CH$_2$OH)$_2$ | OCH$_3$ | OCH$_3$ |
| 7 | 0 | N(CH$_3$CH$_2$CH$_2$N(CH$_3$)$_2$ | OCH$_3$ | OCH$_3$ |
| 8 | 0 | NHC$_3$H$_7$ | OCH$_3$ | OCH$_3$ |
| 9 | 0 | NHCH$_2$C$_6$H$_5$ | OCH$_3$ | OCH$_3$ |

TABLE 1(2)

| Compound | n | NR$^{11}$R$^{12}$ | R$^7$ | R$^8$ |
|---|---|---|---|---|
| 10 | 0 | (morpholino) | OC$_2$H$_5$ | OC$_2$H$_5$ |
| 11 | 0 | (2,6-dimethylmorpholino) | OC$_2$H$_5$ | OC$_2$H$_5$ |

TABLE 1(2)-continued

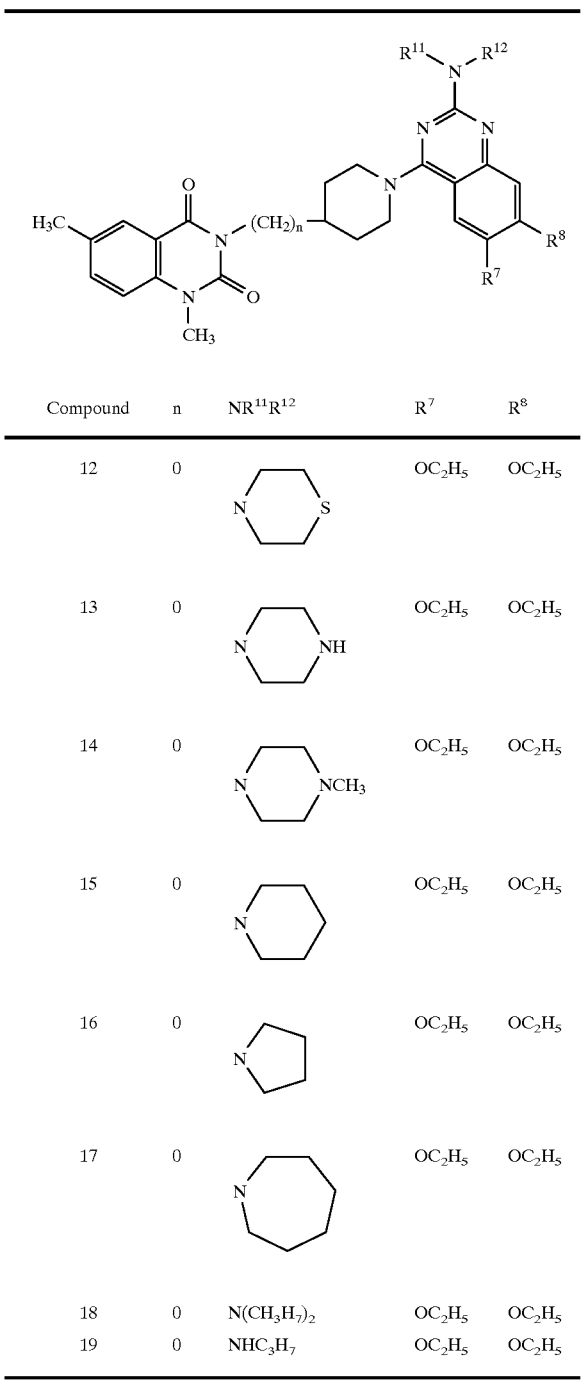

| Compound | n | NR[11]R[12] | R[7] | R[8] |
|---|---|---|---|---|
| 12 | 0 | thiomorpholine | $OC_2H_5$ | $OC_2H_5$ |
| 13 | 0 | piperazine | $OC_2H_5$ | $OC_2H_5$ |
| 14 | 0 | N-methylpiperazine | $OC_2H_5$ | $OC_2H_5$ |
| 15 | 0 | piperidine | $OC_2H_5$ | $OC_2H_5$ |
| 16 | 0 | pyrrolidine | $OC_2H_5$ | $OC_2H_5$ |
| 17 | 0 | azocane | $OC_2H_5$ | $OC_2H_5$ |
| 18 | 0 | $N(C_3H_7)_2$ | $OC_2H_5$ | $OC_2H_5$ |
| 19 | 0 | $NHC_3H_7$ | $OC_2H_5$ | $OC_2H_5$ |

TABLE 1(3)

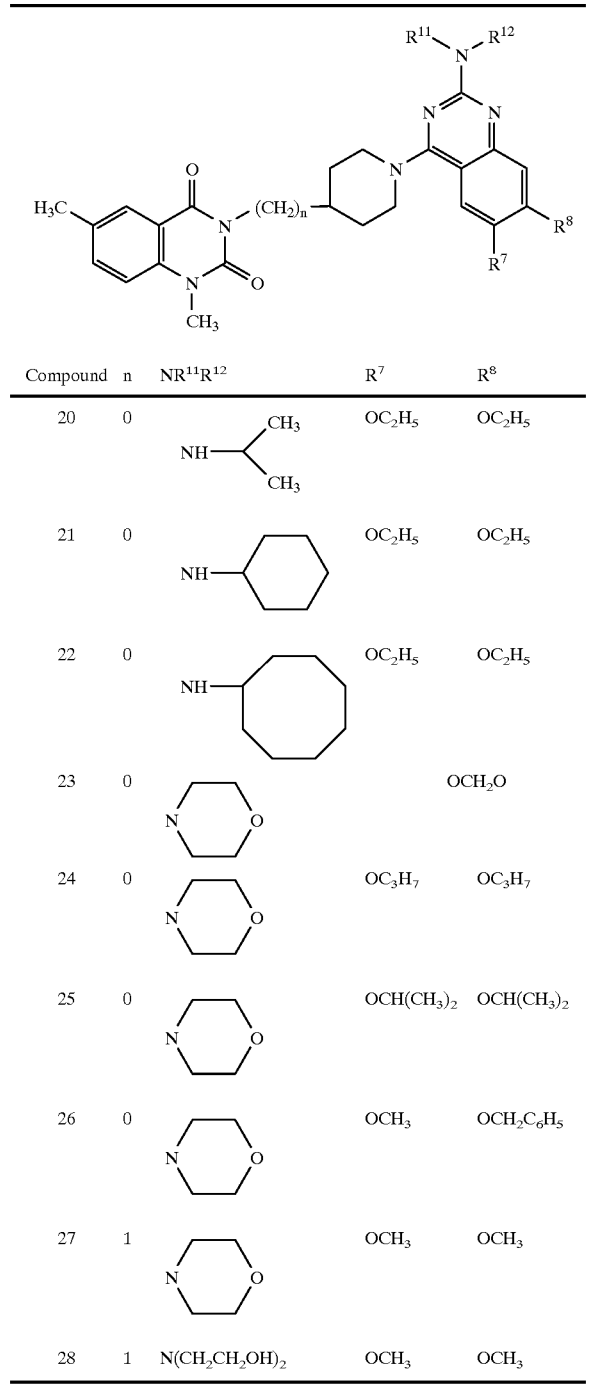

| Compound | n | NR[11]R[12] | R[7] | R[8] |
|---|---|---|---|---|
| 20 | 0 | $NHCH(CH_3)_2$ | $OC_2H_5$ | $OC_2H_5$ |
| 21 | 0 | NH-cyclohexyl | $OC_2H_5$ | $OC_2H_5$ |
| 22 | 0 | NH-cyclooctyl | $OC_2H_5$ | $OC_2H_5$ |
| 23 | 0 | morpholine | $OCH_2O$ | |
| 24 | 0 | morpholine | $OC_3H_7$ | $OC_3H_7$ |
| 25 | 0 | morpholine | $OCH(CH_3)_2$ | $OCH(CH_3)_2$ |
| 26 | 0 | morpholine | $OCH_3$ | $OCH_2C_6H_5$ |
| 27 | 1 | morpholine | $OCH_3$ | $OCH_3$ |
| 28 | 1 | $N(CH_2CH_2OH)_2$ | $OCH_3$ | $OCH_3$ |

TABLE 2

| Compound | n | NR¹¹R¹² | R¹ | R⁷ | R⁸ |
|---|---|---|---|---|---|
| 29 | 2 | morpholino | H | OCH₃ | OCH₃ |
| 30 | 2 | morpholino | CH₃ | OCH₃ | OCH₃ |
| 31 | 2 | N(CH₂CH₂OH)₂ | H | OCH₃ | OCH₃ |

TABLE 3(1)

| Compound | R¹ | R² | R³ | R⁴ | R⁵ |
|---|---|---|---|---|---|
| 32 | H | H | H | H | H |
| 33 | CH₃ | H | H | H | H |
| 34 | H | H | CH₃ | H | H |
| 35 | C₂H₅ | H | CH₃ | H | H |
| 36 | C₃H₇ | H | CH₃ | H | H |
| 37 | H | CH₃ | H | H | H |
| 38 | CH₃ | CH₃ | H | H | H |
| 39 | H | H | H | H | CH₃ |
| 40 | CH₃ | H | H | H | CH₃ |

TABLE 3(2)

| Compound | R¹ | R² | R³ | R⁴ | R⁵ |
|---|---|---|---|---|---|
| 41 | H | H | Cl | H | H |
| 42 | CH₃ | H | Cl | H | H |
| 43 | CH₃ | H | Br | H | H |
| 44 | H | H | NO₂ | H | H |
| 45 | CH₃ | H | NO₂ | H | H |
| 46 | CH₃ | H | CH₃CO | H | H |

TABLE 4(1)

| Compound | R⁷ | R⁸ |
|---|---|---|
| 47 | OC₂H₅ | OH |
| 48 | OC₂H₅ | OCH₃ |
| 49 | OC₂H₅ | O(CH₂)₂CH₃ |
| 50 | OC₂H₅ | OCH(CH₃)₂ |
| 51 | OC₂H₅ | O(CH₂)₃CH₃ |
| 52 | OC₂H₅ | OCOCH₃ |
| 53 | OC₂H₅ | OCH₂CH₂N(CH₃)₂ |
| 54 | OC₂H₅ | OCH₂CO₂CH₂CH₃ |

TABLE 4(2)

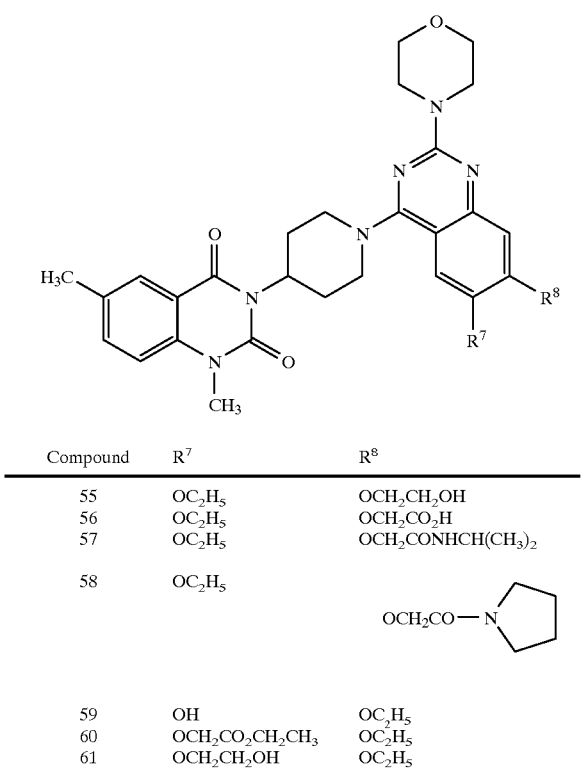

| Compound | R⁷ | R⁸ |
|---|---|---|
| 55 | $OC_2H_5$ | $OCH_2CH_2OH$ |
| 56 | $OC_2H_5$ | $OCH_2CO_2H$ |
| 57 | $OC_2H_5$ | $OCH_2CONHCH(CH_3)_2$ |
| 58 | $OC_2H_5$ | $OCH_2CO-N\text{(pyrrolidine)}$ |
| 59 | OH | $OC_2H_5$ |
| 60 | $OCH_2CO_2CH_2CH_3$ | $OC_2H_5$ |
| 61 | $OCH_2CH_2OH$ | $OC_2H_5$ |

The pharmacological activities of typical Compounds (I) are shown below by Test Examples.

Test Example 1

Inhibitory Effect on [$^3$H]-Adenosine Uptake

A blood sample was obtained from a healthy male adult under 40 years of age by brachial venipuncture using a syringe containing sodium citrate and subjected to centrifugation to obtain washed erythrocytes. To 100 μl of an erythrocyte suspension (2.5×10$^9$/ml) was added 10 μl of a 21% DMSO solution of a test compound. After allowing the suspension to stand at room temperature for 1 hour, 100 μl of a [$^3$H]-adenosine solution was added thereto. Ten seconds later, 200 μl of a dilazep solution (1 mg/ml) was added to stop the reaction. Then, dibutyl phthalate was added dropwise to the reaction mixture, followed by centrifugation. The supernatant was removed and the erythrocyte fraction was separated. The erythrocytes were dissolved in Triton X-100, and the uptake amount of $^3$H was measured with a liquid scintillation counter. The concentration of the test compound which inhibits the [$^3$H]-adenosine uptake by 50% ($IC_{50}$) was calculated. The results obtained are shown in Table 5.

TABLE 5

| Compound No. | [$^3$H]-Adenosine Uptake Inhibition $IC_{50}$ (nM) |
|---|---|
| 1 | 35 |
| 2 | 64 |
| 4 | 72 |
| 6 | 29 |
| 7 | 62 |
| 8 | 50 |
| 10 | 97 |

Test Example 2

Inhibitory Effect on [$^3$H]-Nitrobenzylthioinosine (NBI) Binding (an indication of adenosine uptake inhibitory activity)

The cerebral cortex of a male guinea pig of Hartley strain was homogenized with an ice-cooled 50 mM tris-HCl buffer (pH 7.4) in an amount of 25 times (w/v) that of the tissue. The homogenate was centrifuged (30,000×g, 4° C., 20 mins.), and the supernatant was discarded. To the precipitate was added the same amount of the buffer, followed by homogenization and then centrifugation in the same manner as above. The obtained precipitate was suspended in 20 times as much buffer as the precipitate to prepare a suspension for testing.

To a DMSO solution of a test compound were added 1.5 nM of [$^3$H]-NBI and 5 mg (wet basis) of the tissue homogenate, and the mixture was allowed to stand at 25° C. for 30 minutes. To the mixture was added 4 ml of an ice-cooled buffer, followed by rapid filtration with suction through a glass filter (GF/C, produced by Whatman Ltd.) or a Ready filter (produced by Beckman Co.) to stop the reaction. The filter was transferred to a scintillation vial, and after drying, Scintisol EX-H was added thereto. The radioactivity was measured with a liquid scintillation counter. The binding inhibitory activity was expressed in terms of an inhibition constant (Ki value) as calculated according to Cheng-Prusoff's formula. The results obtained are shown in Table 6 below.

TABLE 6

| Compound No. | [$^3$H]-NBI Binding Ki Value (nM) |
|---|---|
| 1 | 2.0 |
| 3 | 7.6 |
| 5 | 2.6 |
| 6 | 1.5 |
| 7 | 3.8 |
| 8 | 1.4 |
| 10 | 2.0 |

Test Example 3

Acute Toxicity Test

A test compound was orally or intraperitoneally administered to groups of dd-strain male mice weighing 20±1 g, each group consisting of three mice. Seven days after the administration, the mortality was observed to determine a minimum lethal dose (MLD) of the compound. The MLD was >1000 mg/kg for oral administration of Compound 10 and was >100 mg/kg for intraperitoneal administration of Compound 10.

Test Example 4

Effect on Increase of Albumin Excretion in Masugi Nephritis

Mouse nephrotoxin (hereinafter referred to as NT) was prepared according to the method of Ito, et al. [The Japanese Journal of Nephrology, 23, 25–36 (1981)]. That is, glomerular basement membrane (hereinafter referred to as GBM) was isolated from mouse kidney and digested with trypsin (Sigma). The digested GBM was subjected to ultracentrifugation under cooling, and the supernatant was dialyzed against distilled water, followed by lyophilization. The lyophile product was intracutaneously injected as an antigen into four foot pads of a rabbit together with Freund's complete adjuvant (Iatron; hereinafter referred to as FCA) once a week for 4 weeks for immunization. The whole blood was drawn from the immunized rabbit, and serum was separated and inactivated at 56° C. for 30 minutes to prepare NT.

In this test, ddY-strain male mice weighing 29–36 g were used. For previous immunization, 0.25 ml of an FCA emulsion containing 0.25 mg of rabbit immunoglobulin-globulin (IgG, Sigma) was intraperitoneally injected into mice. Nephritis was induced by intravenous injection of 0.075 ml of NT through the tail vein 4 and 11 days after the previous immunization. Four weeks after the second NT injection, each mouse was put into a metabolic cage and received oral administration of 0.5 ml/10 g of distilled water twice at an interval of 12 hours. Urine was collected for 24 hours, and after measurement of the volume, the urine was centrifuged under cooling (3000 rpm, 4° C.) for 5 minutes. The supernatant was analyzed for albumin using an autoanalyzer (Olympus). A test compound was orally administered at a dose of 1 mg/kg once a day, starting on the day of the previous immunization. The normal group and the control group received oral administration of a solvent (5% methyl cellulose solution) at the same time.

The results are shown in Table 7 as the means±standard error of each group consisting of 11 mice. Statistical significance was evaluated by Student's t-test.

TABLE 7

| Test Group | Urinary Albumin Content (mg/kg/24 hr) |
|---|---|
| Normal group | 85 ± 5** |
| Control group | 134 ± 9 |
| Compound 10-administered group | 96 ± 7** |

It is apparent from the above test results that Compound 10 inhibits the increase of urinary albumin in nephritis and thus is useful for the treatment of nephritis.

Test Example 5

Effect on Increase of Albumin Excretion in Diabetic Nephropathy

In this test, ddY-strain male mice weighing 25–28 g were used. Diabetes was induced according to the method of Tsuchida, et al. [Jin To Toseki (Kidney and Dialysis), 31, 363–366 (1991)]. That is, streptozotocin (5 mg/ml, Sigma; hereinafter referred to as STZ) dissolved in 0.05 M citrate buffer was intravenously injected into mice through the tail vein at a dose of 10 ml/kg. On the fourth day after the STZ administration, 30 μl of blood was collected from the tail vein of the mice and the blood glucose was determined using Glutestsensor (Sanwa Kagaku). The animals were divided into three groups based on the blood glucose level. Twelve weeks after the STZ administration, each mouse was put into a metabolic cage and received oral administration of 0.5 ml/10 g of distilled water twice at an interval of 12 hours. Urine was collected for 24 hours, and after measurement of the volume, the urine was centrifuged under cooling (3000 rpm, 4° C. ) for 5 minutes. The supernatant was analyzed for albumin using an autoanalyzer (Olympus). A test compound was orally administered once a day for 11 weeks, starting on the fifth day after the STZ administration. The normal group and the control group received oral administration of a solvent (5% methyl cellulose solution).

The results are shown in Table 8 as the means standard error of each group. Statistical significance was evaluated by Aspin-Welch's test for the difference between the control group and the normal group and by Steel's test for the difference between the control group and the test compound-administered group.

TABLE 8

| Test Group | Number of Animals | Urinary Albumin Content (mg/kg/24 hr) |
|---|---|---|
| Normal group | 10 | 80 ± 3*** |
| Control group | 8 | 333 ± 30 |
| Compound 10-administered group | | |
| (1 mg/kg) | 10 | 244 ± 16* |
| (10 mg/kg) | 9 | 200 ± 13** |

*; ; *: The data differed significantly from that on the control group respectively at the less than 5%, less than 1%, and less than 0.1% levels.

It is apparent from the above test results that Compound 10 inhibits the increase of urinary albumin in diabetic nephropathy and thus is useful for the treatment of diabetic nephropathy.

Compounds (I) and pharmaceutically acceptable salts thereof can be formulated into generally employed dose forms, such as tablets, capsules, syrups, injections, drips, and suppositories, and administered orally or non-orally through intramuscular injection, intravenous injection, intraarterial injection, drip infusion, or rectal administration in the form of suppositories. For preparing these dose forms for oral or non-oral administration, generally known methods are applied. For example, the preparations may be formulated to contain various excipients, lubricants, binders, disintegrating agents, suspending agents, isotonizing agents, emulsifiers, and the like.

Examples of the carriers which can be used are water, injectable distilled water, physiological saline, glucose, fructose, sucrose, mannitol, lactose, starch, cellulose, methyl cellulose, carboxymethyl cellulose, hydroxypropyl cellulose, alginic acid, talc, sodium citrate, calcium carbonate, calcium hydrogenphosphate, magnesium stearate, urea, silicone resins, sorbitan fatty acid esters, and glycerin fatty acid esters.

The dose will vary depending upon the mode of administration, the age, body weight, and symptoms of a patient, etc. However, it is generally appropriate to administer Compound (I) or a pharmaceutically acceptable salt thereof in a dose of 1 to 900 mg/60 kg/day either orally or non-orally.

Certain embodiments of the present invention are illustrated in the following Examples and Reference Examples.

EXAMPLE 1

3-[1-(6,7-Dimethoxy-2-morpholino-4-quinazolinyl)-4-piperidinyl]-1,2,3,4-tetrahydro-1,6-dimethyl-2,4-dioxoquinazoline (Compound 1)

In 15 ml of dimethylformamide was dissolved 200 mg (0.40 mmol) of 3-[1-(2-chloro-6,7-dimethoxy-4- quinazolinyl)-4-piperidinyl]-1,2,3,4-tetrahydro-1,6-dimethyl-2,4-dioxoquinazoline (Compound a) obtained in Reference Example 1, and 0.18 ml (2.0 mmol) of morpholine and 0.17 ml (1.2 mmol) of triethylamine were added to the solution. The mixture was heated under reflux at 130° C. for 5 hours. After the solvent was evaporated, water was added to the residue, followed by extraction with chloroform. The organic layer was washed and dried, and the solvent was evaporated. The residue was purified by silica gel column chromatography (solvent: chloroform/methanol=50/1) and recrystallization from ethyl acetate and ether to give 75.6 mg (yield: 35%) of Compound 1 as white crystals.

$^1$H-NMR (CDCl$_3$) δ: 8.01 (d, 1H, J=2.0 Hz), 7.48 (dd, 1H, J=8.6, 2.0 Hz), 7.09 (d, 1H, J=8.6 Hz), 7.08 (s, 1H), 6.96 (s, 1H), 5.30–5.15 (m, 1H), 4.27–4.24 (br.-d, 2H), 3.98 (s, 3H), 3.93 (s, 3H), 3.83–3.81 (m, 8H), 3.58 (s, 3H), 3.15–3.00 (m, 4H), 2.42 (s, 3H), 1.81–1.78 (br.-d, 2H).

IR (KBr tab.)(cm$^{-1}$): 1702, 1653, 1482, 1232, 1207.

Melting Point (ethyl acetate-ether): 256–257° C.

EXAMPLE 2

3-{1-[6,7-Dimethoxy-2-(4-methyl-1-piperazinyl)-4-quinazolinyl]-4-piperidinyl}-1,2,3,4-tetrahydro-1,6-dimethyl-2,4-dioxoquinazoline (Compound 2)

The same procedure as in Example 1 was repeated, except that 300 mg (0.63 mmol) of Compound a was used and 0.4 ml (3.25 mmol) of N-methylpiperazine was used in place of morpholine, to give 97.3 mg (yield: 27%) of Compound 2 as white crystals.

$^1$H-NMR (CDCl$_3$) δ: 8.02 (d, 1H, J=2.0 Hz), 7.48 (dd, 1H, J=8.6, 2.0 Hz), 7.08 (d, 1H, J=8.6 Hz), 7.07 (s, 1H), 6.94 (s, 1H), 5.30–5.15 (m, 1H), 4.26–4.23 (br.-d, 2H), 3.97 (s, 3H), 3.93 (s, 3H), 3.93–3.90 (m, 4H), 3.58 (s, 3H), 3.10–3.02 (m, 4H), 2.52–2.49 (m, 4H), 2.42 (s, 3H), 2.36 (s, 3H), 1.82–1.79 (br.-d, 2H).

IR (KBr tab.)(cm$^{-1}$): 1704, 1656, 1509.

Melting Point: (ethyl acetate-ether-hexane): 168–171° C.

EXAMPLE 3

3-{1-[2-(4-Ethoxycarbonylpiperidino)-6,7-dimethoxy-4-quinazolinyl]-4-piperidinyl}-1,2,3,4-tetrahydro-1,6-dimethyl-2,4-dioxoquinazoline (Compound 3)

The same procedure as in Example 1 was repeated, except that 600 mg (1.25 mmol) of Compound a was used, N-methylpyrrolidinone was used as the solvent in place of dimethylformamide, and 1.9 ml (12.5 mmol) of ethyl isonipecotate was used in place of morpholine, to give 760.0 mg (yield: 99%) of Compound 3 as white crystals.

$^1$H-NMR (CDCl$_3$) δ: 8.02 (d, 1H, J=2.0 Hz), 7.48 (dd, 1H, J=8.3, 2.0 Hz), 7.08 (d, 1H, J=8.3 Hz), 7.06 (s, 1H), 6.93 (s, 1H), 5.30–5.15 (m, 1H), 4.80–4.74 (br.-d, 2H), 4.25–4.21 (br.-d, 2H), 4.15 (q, 2H, J=7.3 Hz), 3.98 (s, 3H), 3.93 (s, 3H), 3.58 (s, 3H), 3.09–2.85 (m, 6H), 2.60–2.45 (m, 1H), 2.42 (s, 3H), 2.02–1.98 (br.-d, 2H), 1.82–1.63 (m, 4H), 1.27 (t, 3H, J=7.3 Hz).

IR (KBr tab.)(cm$^{-1}$): 1699, 1656, 1459.

Melting Point: (methanol-water): 103–105° C.

EXAMPLE 4

3-{1-[2-(4-Carboxypiperidino)-6,7-dimethoxy-4-quinazolinyl]-4-piperidinyl}-1,2,3,4-tetrahydro-1,6-dimethyl-2,4-dioxoquinazoline (Compound 4)

In 10 ml of methanol was dissolved 400 mg (0.65 mmol) of Compound 3 obtained in Example 3, and 5 ml of 2 N aqueous solution of sodium hydroxide was added to the solution, followed by heating under reflux for one hour. After cooling, the solvent was evaporated, and water and concentrated hydrochloric acid were added to the residue. The precipitated crystals were collected by filtration, and then washed with water and methanol to give 308.0 mg (yield: 81%) of Compound 4 as white crystals.

$^1$H-NMR (CDCl$_3$) δ: 7.98 (d, 1H, J=1.0 Hz), 7.45 (dd, 1H, J=7.0, 1.0 Hz), 7.06 (s, 1H), 7.04 (d, 1H, J=7.0 Hz), 7.01 (s, 1H), 5.30–5.15 (m, 1H), 4.71–4.67 (br.-d, 2H), 4.29–4.25 (br.-d, 2H), 3.95 (s, 3H), 3.90 (s, 3H), 3.55 (s, 3H), 3.10–3.01 (m, 6H), 2.60–2.40 (m, 1H), 2.40 (s, 3H), 2.05–1.99 (br.-d, 2H), 1.85–1.65 (m, 4H).

IR (KBr tab.)(cm$^{-1}$): 3400 (br), 1700, 1654, 1639, 1521.

Melting Point (methanol-water): 189–190° C.

EXAMPLE 5

3-[1-(2-Dimethylamino-6,7-dimethoxy-4-quinazolinyl)-4-piperidinyl]-1,2,3,4-tetrahydro-1,6-dimethyl-2,4-dioxoquinazoline (Compound 5)

The same procedure as in Example 1 was repeated, except that 300 mg (0.63 mmol) of Compound a was used and 0.3 ml (3.25 mmol) of propylamine was used in place of morpholine, to give 143.0 mg (yield: 42.4%) of Compound 5 as white crystals.

$^1$H-NMR (CDCl$_3$) δ: 8.01 (d, 1H, J=2.0 Hz), 7.48 (dd, 1H, J=8.3, 2.0 Hz), 7.08 (d, 1H, J=8.3 Hz), 7.07 (s, 1H), 6.95 (s, 1H), 5.30–5.15 (m, 1H), 4.26–4.23 (br.-d, 2H), 3.97 (s, 3H), 3.93 (s, 3H), 3.57 (s, 3H), 3.24 (s, 6H), 3.10–3.01 (m, 4H), 2.42 (s, 3H), 1.81–1.78 (br.-d, 2H).

IR (KBr tab.)(cm$^{-1}$): 1695, 1656, 1553, 1512, 1503.

Melting Point (ethyl acetate-ether): 220–221° C.

EXAMPLE 6

3-{1-[2-Bis(2-hydroxyethyl)amino-6,7-dimethoxy-4-quinazolinyl]-4-piperidinyl}-1,2,3,4-tetrahydro-1,6-dimethyl-2,4-dioxoquinazoline (Compound 6)

The same procedure as in Example 1 was repeated, except that 500 mg (1.04 mmol) of Compound a was used, N-methylpyrrolidinone was used as the solvent in place of dimethylformamide, and 1.0 ml (10 mmol) of diethanolamine was used in place of morpholine, to give 163.5 mg (yield: 28%) of Compound 6 as white crystals.

$^1$H-NMR (CDCl$_3$) δ: 8.01 (d, 1H, J=2.0 Hz), 7.48 (dd, 1H, J=8.3, 2.0 Hz), 7.09 (d, 1H, J=8.3 Hz), 7.04 (s, 1H), 6.84 (s, 1H), 5.30–5.15 (m, 1H), 4.25–4.20 (br.-d, 2H), 3.96 (s, 3H), 3.92 (s, 3H), 3.92–3.84 (m, 8H), 3.56 (s, 3H), 3.19–3.00 (m, 4H), 2.42 (s, 3H), 1.84–1.80 (br.-d, 2H).

IR (KBr tab.)(cm$^{-1}$): 3400 (br), 1698, 1656, 1498.

Melting Point (ethyl acetate-ether): 157–161° C.

EXAMPLE 7

3-{1-{2-[N-(2-Dimethylaminoethyl)-N-methylamino]-6,7-dimethoxy-4-quinazolinyl}-4-piperidinyl}-1,2,3,4-tetrahydro-1,6-dimethyl-2,4-dioxoquinazoline (Compound 7)

The same procedure as in Example 1 was repeated, except that 300 mg (0.63 mmol) of Compound a was used and 0.4 ml (3.2 mmol) of N,N,N'-trimethylethylenediamine was used in place of morpholine, to give 86.3 mg (yield: 24%) of Compound 7 as an amorphous solid.

$^1$H-NMR (CDCl$_3$) δ: 8.01 (d, 1H, J=2.0 Hz), 7.48 (dd, 1H, J=8.2, 2.0 Hz), 7.08 (d, 1H, J=8.2 Hz), 7.06 (s, 1H), 6.97 (s, 1H), 5.30–5.15 (m, 1H), 4.26–4.22 (br.-d, 2H), 3.98 (s, 3H), 3.93 (s, 3H), 3.86 (t, 2H, J=7.3 Hz), 3.58 (s, 3H), 3.25 (s, 3H), 3.11–3.00 (m, 4H), 2.63 (t, 2H, J=7.3 Hz), 2.42 (s, 3H), 2.37 (s, 6H), 1.80–1.77 (br.-d, 2H).

IR (KBr tab.)(cm$^{-1}$): 1700, 1656, 1509.

EXAMPLE 8

3-[1-(6,7-Dimethoxy-2-propylamino-4-quinazolinyl)-4-piperidinyl]- 1,2,3,4-tetrahydro-1,6-dimethyl-2,4-dioxoquinazoline (Compound 8)

The same procedure as in Example 1 was repeated, except that 300 mg (0.63 mmol) of Compound a was used, N-methylpyrrolidinone was used as the solvent in place of dimethylformamide, and 0.3 ml (3.2 mmol) of propylamine was used in place of morpholine, to give 124.5 mg (yield: 37%) of Compound 8 as white crystals.

$^1$H-NMR (CDCl$_3$) δ: 8.02 (d, 1H, J=2.0 Hz), 7.49 (dd, 1H, J=8.6, 2.0 Hz), 7.09 (d, 1H, J=8.6 Hz), 7.08 (s, 1H), 6.94 (s, 1H), 5.32–5.23 (m, 1H), 4.38–4.34 (br.-d, 2H), 3.98 (s, 3H), 3.92 (s, 3H), 3.58 (s, 3H), 3.52–3.38 (m, 2H), 3.21–3.00 (m, 4H), 2.42 (s, 3H), 1.86–1.82 (br.-d, 2H), 1.67 (sext, 2H, J=7.4 Hz), 1.01 (t, 3H, J=7.4 Hz).

IR (KBr tab.)(cm$^{-1}$): 1703, 1654, 1508.

Melting Point (ethyl acetate-ether): 156–160° C.

EXAMPLE 9

3-[1-(2-Benzylamino-6,7-dimethoxy-4-quinazolinyl)-4-piperidinyl]-1,2,3,4-tetrahydro-1,6-dimethyl-2,4-dioxoquinazoline (Compound 9)

The same procedure as in Example 1 was repeated, except that 500 mg (1.04 mmol) of Compound a was used, N-methylpyrrolidinone was used as the solvent in place of dimethylformamide, and 0.5 ml (5.2 mmol) of benzylamine was used in place of morpholine, to give 31.8 mg (yield: 5.7%) of Compound 9 as white crystals.

$^1$H-NMR (CDCl$_3$) δ: 8.01 (d, 1H, J=1.5 Hz), 7.51–7.22 (m, 6H), 7.09 (d, 1H, J=8.5 Hz), 7.08 (s, 1H), 6.96 (s, 1H), 5.30–5.15 (m, 1H), 4.71 (d, 2H, J=6.6 Hz), 4.34–4.29 (br.-d, 2H), 3.99 (s, 3H), 3.93 (s, 3H), 3.58 (s, 3H), 3.13–2.97 (m, 4H), 2.42 (s, 3H), 1.82–1.78 (br.-d, 2H).

IR (KBr tab.)(cm$^{-1}$): 1703, 1659, 1560, 1511.

Melting Point (ethyl acetate-ether): 136–139° C.

EXAMPLE 10

3-[1-(6,7-Diethoxy-2-morpholino-4-quinazolinyl)-4-piperidinyl]-1,2,3,4-tetrahydro-1,6-dimethyl-2,4-dioxoquinazoline hydrochloride (Compound 10)

Step 1:

The same procedure as in Example 1 was repeated, except that 3.60 g (7.09 mmol) of 3-[1-(2-chloro-6,7-diethoxy-4-quinazolinyl)-4-piperidinyl]-1,2,3,4-tetrahydro-1,6-dimethyl-2,4-dioxoquinazoline (Compound b) obtained in Reference Example 2 was used in place of Compound a, and N-methylpyrrolidinone was used as the solvent in place of dimethylformamide, to give 3.47 g (yield: 85%) of the free base of Compound 10 as white crystals.

$^1$H-NMR (CDCl$_3$) δ: 8.01 (d, 1H, J=1.5 Hz), 7.49 (dd, 1H, J=8.5, 1.5 Hz), 7.11 (s, 1H), 7.08 (d, 1H, J=8.5 Hz), 6.97 (s, 1H), 5.30–5.20 (m, 1H), 4.28–4.24 (br.-d, 2H), 4.20 (q, 2H, J=7.0 Hz), 4.12 (q, 2H, J=7.0 Hz), 3.84–3.81 (m, 8H), 3.58 (s, 3H), 3.20–2.95 (m, 4H), 2.42 (s, 3H), 1.85–1.81 (br.-d, 2H), 1.51 (t, 3H, J=7.0 Hz), 1.49 (t, 3H, J=7.0 Hz).

IR (KBr tab.)(cm$^{-1}$): 1699, 1656, 1563, 1459, 1237, 1180, 1109.

Melting Point (ether): 228–229° C.

Step 2:

In 20 ml of ethyl acetate was dissolved 1.0 g (1.74 mmol) of the free base obtained in Step 1, and an excess of a saturated solution of hydrogen chloride in ethyl acetate was added dropwise to the solution at room temperature, followed by stirring for 10 minutes. The precipitated crystals were collected by filtration, and washed with ethyl acetate to give 0.87 g (yield: 82%) of Compound 10 as white crystals.

$^1$H-NMR (CDCl$_3$) δ: 8.49 (br-s, 1H), 8.00 (s, 1H), 7.50 (d, 1H, J=8.5 Hz), 7.11 (d, 1H, J=8.5 Hz), 7.07 (s, 1H), 5.45–5.30 (m, 1H), 4.66–4.61 (br.-d, 2H), 4.34–4.32 (br.-d, 2H), 4.13–4.08 (m, 6H), 3.84 (br.-s, 4H), 3.57 (s, 3H), 3.57 (s, 3H), 3.40–3.31 (br.-t, 2H), 3.01–2.89 (m, 2H), 2.43 (s, 3H), 1.92–1.88 (br.-d, 2H), 1.50 (t, 3H, J=7.0 Hz), 1.48 (t, 3H, J=7.0 Hz).

Melting Point (ethyl acetate): 193–195° C.

EXAMPLE 11

3-{1-[2-(cis-2,6-Dimethylmorpholino)-6,7-diethoxy-4-quinazolinyl]-4-piperidinyl}-1,2,3,4-tetrahydro-1, 6-dimethyl-2,4-dioxoquinazoline hydrochloride (Compound 11)

The same procedure as in Example 10 was repeated, except that 2,6-dimethylmorpholine (trans-cis mixture) was used in place of morpholine, to give Compound 11 as white crystals.

$^1$H-NMR (CDCl$_3$) δ: 8.01 (d, 1H, J=1.5 Hz), 7.48 (dd, 1H, J=8.5, 1.5 Hz), 7.10 (s, 1H), 7.08 (d, 1H, J=8.5 Hz), 6.92 (s, 1H), 5.30–5.15 (m, 1H), 4.66–4.61 (br.-d, 2H), 4.21–4.07 (m, 6H), 3.70–3.69 (m, 2H), 3.58 (s, 3H), 3.10–2.99 (m, 4H), 2.65–2.55 (br.-t, 2H), 2.42 (s, 3H), 1.82–1.76 (br.-d, 2H), 1.51 (t, 3H, J=7.0 Hz), 1.49 (t, 3H, J=7.0 Hz), 1.28 (d, 6H, J=6.0 Hz). (as the free base)

IR (KBr tab.)(cm$^{-1}$): 1702, 1658, 1591, 1460, 1262.

Melting Point (ether): 241–242° C.

EXAMPLE 12

3-[1-(6,7-Diethoxy-2-thiomorpholino-4-quinazolinyl)-4-piperidinyl]-1,2,3,4-tetrahydro-1,6-dimethyl-2,4-dioxoquinazoline hydrochloride (Compound 12)

The same procedure as in Example 10 was repeated, except that thiomorpholine was used in place of morpholine, to give Compound 12 as white crystals.

$^1$H-NMR (CDCl$_3$) δ: 8.01 (d, 1H, J=1.5 Hz), 7.49 (dd, 1H, J=8.5, 1.5 Hz), 7.09 (s, 1H), 7.09 (d, 1H, J=8.5 Hz), 6.90 (s, 1H), 5.25–5.10 (m, 1H), 4.25–4.08 (m, 10H), 3.58 (s, 3H), 3.10–2.99 (m, 4H), 2.80–2.60 (m, 4H), 2.42 (s, 3H), 1.81–1.77 (br.-d, 2H), 1.51 (t, 3H, J=7.0 Hz), 1.49 (t, 3H, J=7.0 Hz). (as the free base)

IR (KBr tab.)(cm$^{-1}$): 1698, 1657, 1587, 1458, 1270.

Melting Point (ether): 179–182° C.

EXAMPLE 13

3-{1-[6,7-Diethoxy-2-(1-piperazinyl)-4-quinazolinyl]-4-piperidinyl}-1,2,3,4-tetrahydro-1,6-dimethyl-2,4-dioxoquinazoline dihydrochloride (Compound 13)

The same procedure as in Example 10 was repeated, except that piperazine was used in place of morpholine, to give Compound 13 as a colorless amorphous solid.

¹H-NMR (CDCl₃) δ: 8.02 (d, 1H, J=1.5 Hz), 7.48 (dd, 1H, J=8.5, 1.5 Hz), 7.10 (s, 1H), 7.09 (d, 1H, J=8.5 Hz), 7.00 (s, 1H), 5.35–5.10 (m, 1H), 4.29–4.24 (br.-d, 2H), 4.20 (q, 2H, J=7.0 Hz), 4.13 (q, 2H, J=7.0 Hz), 4.10–4.00 (m, 4H), 3.58 (s, 3H), 3.17–2.99 (m, 8H), 2.42 (s, 3H), 1.81–1.76 (br.-d, 2H), 1.52 (t, 3H, J=7.0 Hz), 1.49 (t, 3H, J=7.0 Hz). (as the free base)

IR (KBr tab.)(cm⁻¹): 1701, 1656, 1651, 1626, 1585, 1459, 1257.

EXAMPLE 14

3-{1-[6,7-Diethoxy-2-(4-methyl-1-piperazinyl)- 4-quinazolinyl]-4-piperidinyl}-1,2,3,4-tetrahydro-1,6-dimethyl-2,4-dioxoquinazoline dimethanesulfonate (Compound 14)

The same procedure as in Example 10 was repeated, except that N-methylpiperazine was used in place of morpholine in Step 1 and methanesulfonic acid was used in place of a saturated solution of hydrogen chloride in Step 2, to give Compound 14 as white crystals.

¹H-NMR (CDCl₃) δ: 8.01 (d, 1H, J=1.5 Hz), 7.48 (dd, 1H, J=8.3, 1.5 Hz), 7.10 (s, 1H), 7.08 (d, 1H, J=8.3 Hz), 6.92 (s, 1H), 5.30–5.15 (m, 1H), 4.25–4.23 (br.-d, 2H), 4.19 (q, 2H, J=7.0 Hz), 4.12 (q, 2H, J=7.0 Hz), 3.89–3.83 (m, 4H), 3.58 (s, 3H), 3.08–2.96 (m, 4H), 2.51–2.48 (m, 4H), 2.41 (s, 3H), 2.34 (s, 3H), 1.81–1.78 (br.-d, 2H), 1.51 (t, 3H, J=7.0 Hz), 1.48 (t, 3H, J=7.0 Hz). (as the free base)

IR (KBr tab.)(cm⁻¹): 1705, 1658, 1637, 1195.

Melting Point (ethyl acetate-ether): 187–189° C.

EXAMPLE 15

3-[1-(6,7-Diethoxy-2-piperidino-4-quinazolinyl)-4-piperidinyl]-1,2,3,4-tetrahydro-1,6-dimethyl-2,4-dioxoquinazoline hydrochloride (Compound 15)

The same procedure as in Example 10 was repeated, except that piperidine was used in place of morpholine, to give Compound 15 as white crystals.

¹H-NMR (CDCl₃) δ: 8.02 (d, 1H, J=1.5 Hz), 7.48 (dd, 1H, J=8.5, 1.5 Hz), 7.09 (s, 1H), 7.09 (d, 1H, J=8.5 Hz), 6.90 (br.-s, 1H), 5.30–5.15 (m, 1H), 4.30–4.05 (m, 6H), 3.90–3.75 (m, 4H), 3.58 (s, 3H), 3.15–2.95 (m, 4H), 2.42 (s, 3H), 1.81–1.75 (br.-d, 2H), 1.64–1.53 (m, 6H), 1.51 (t, 3H, J=7.0 Hz), 1.48 (t, 3H, J=7.0 Hz). (as the free base);

IR (KBr tab.)(cm⁻¹): 1706, 1648, 1586, 1459, 1271.

Melting Point (ethanol-ether): 189–191° C.

EXAMPLE 16

3-{1-[6,7-Diethoxy-2-(1-pyrrolidinyl)-4-quinazolinyl]-4-piperidinyl}-1,2,3,4-tetrahydro-1,6-dimethyl-2,4-dioxoquinazoline hydrochloride (Compound 16)

The same procedure as in Example 10 was repeated, except that pyrrolidine was used in place of morpholine, to give Compound 16 as white crystals.

¹H-NMR (CDCl₃) δ: 8.02 (d, 1H, J=1.5 Hz), 7.48 (dd, 1H, J=8.5, 1.5 Hz), 7.10 (s, 1H), 7.08 (d, 1H, J=8.5 Hz), 6.95 (br.-s, 1H), 5.30–5.15 (m, 1H), 4.40–4.24 (m, 2H), 4.20 (q, 2H, J=7.0 Hz), 4.11 (q, 2H, J=7.0 Hz), 3.70–3.50 (m, 4H), 3.58 (s, 3H), 3.08–2.99 (m, 4H), 2.42 (s, 3H), 2.00–1.96 (m, 4H), 1.80–1.77 (br.-d, 2H), 1.50 (t, 3H, J=7.0 Hz), 1.48 (t, 3H, J=7.0 Hz). (as the free base)

IR (KBr tab.)(cm⁻¹): 1706, 1648, 1626, 1601, 1538, 1462, 1270.

Melting Point (ether): 220–222° C.

EXAMPLE 17

3-[1-(6,7-Diethoxy-2-hexamethyleneimino-4-quinazolinyl)-4-piperidinyl]-1,2,3,4-tetrahydro-1,6-dimethyl-2,4-dioxoquinazoline hydrochloride (Compound 17)

The same procedure as in Example 10 was repeated, except that hexamethyleneimine was used in place of morpholine, to give Compound 17 as white crystals.

¹H-NMR (CDCl₃) δ: 8.01 (d, 1H, J=2.0 Hz), 7.48 (dd, 1H, J=8.6, 2.0 Hz), 7.10 (s, 1H), 7.08 (d, 1H, J=8.6 Hz), 35 6.90 (br.-s, 1H), 5.30–5.10 (m, 1H), 4.21–4.14 (m, 4H), 4.10 (q, 2H, J=7.0 Hz), 3.90–3.70 (m, 4H), 3.58 (s, 3H), 3.07–2.95 (m, 4H), 2.42 (s, 3H), 1.95–1.80 (m, 6H), 1.56–1.40 (m, 4H), 1.50 (t, 3H, J=7.0 Hz), 1.47 (t, 3H, J=7.0 Hz). (as the free base)

IR (KBr tab.)(cm⁻¹): 1700, 1660, 1650, 1592.

Melting Point (ether): 154–163° C.

EXAMPLE 18

3-[1-(2-Dipropylamino-6,7-diethoxy-4-quinazolinyl)-4-piperidinyl]-1,2,3,4-tetrahydro-1,6-dimethyl-2,4-dioxoquinazoline hydrochloride (Compound 18)

The same procedure as in Example 10 was repeated, except that dipropylamine was used in place of morpholine, to give Compound 18 as white crystals.

¹H-NMR (CDCl₃) δ: 8.02 (d, 1H, J=1.5 Hz), 7.48 (dd, 1H, J=8.5, 1.5 Hz), 7.09 (s, 1H), 7.09 (d, 1H, J=8.5 Hz), 6.88 (s, 1H), 5.30–5.15 (m, 1H), 4.21–4.18 (br.-d, 2H), 4.18 (q, 2H, J=7.0 Hz), 4.10 (q, 2H, J=7.0 Hz), 3.65–3.50 (m, 4H), 3.57 (s, 3H), 3.10–2.95 (m, 4H), 2.42 (s, 3H), 1.80–1.66 (m, 6H), 1.50 (t, 3H, J=7.0 Hz), 1.48 (t, 3H, J=7.0 Hz), 0.95–0.91 (dist.-t, 6H). (as the free base)

IR (KBr tab.)(cm⁻¹): 1708, 1659, 1627, 1593, 1543, 1361.

Melting Point (ether): 240–242° C.

EXAMPLE 19

3-[1-(6,7-Diethoxy-2-propylamino-4-quinazolinyl)-4-piperidinyl]-1,2,3,4-tetrahydro-1,6-dimethyl-2,4-dioxoquinazoline hydrochloride (Compound 19)

The same procedure as in Example 10 was repeated, except that propylamine was used in place of morpholine, to give Compound 19 as white crystals.

¹H-NMR (CDCl₃) δ: 8.01 (d, 1H, J=1.5 Hz), 7.49 (dd, 1H, J=8.3, 1.5 Hz), 7.10 (d, 1H, J=8.3 Hz), 7.09 (s, 1H), 6.93 (s, 1H), 5.40–5.20 (m, 1H), 4.52–4.48 (br.-d, 2H), 4.20 (q, 2H, J=7.0 Hz), 4.09 (q, 2H, J=7.0 Hz), 3.58 (s, 3H), 3.47–3.40 (m, 2H), 3.29–3.19 (br.-t, 2H), 3.04–2.97 (m, 2H), 2.42 (s, 3H), 1.88–1.84 (br.-d, 2H), 1.67 (sext, 2H, J=7.0 Hz), 1.50 (t, 3H, J=7.0 Hz), 1.48 (t, 3H, J=7.0 Hz), 1.00 (t, 3H, J=7.0 Hz). (as the free base)

IR (KBr tab.)(cm⁻¹): 1702, 1657, 1524.

Melting Point (ether): 225–227° C.

EXAMPLE 20

3-[1-(6,7-Diethoxy-2-isopropylamino-4-quinazolinyl)-4-piperidinyl]-1,2,3,4-tetrahydro-1,6-dimethyl-2,4-dioxoquinazoline hydrochloride (Compound 20)

The same procedure as in Example 10 was repeated, except that isopropylamine was used in place of morpholine, to give Compound 20 as white crystals.

¹H-NMR (CDCl₃) δ: 8.00 (d, 1H, J=1.5 Hz), 7.50 (dd, 1H, J=8.5, 1.5 Hz), 7.10 (d, 1H, J=8.5 Hz), 7.08 (s, 1H), 6.99 (br.-s, 1H), 5.40–5.20 (m, 1H), 4.70–4.65 (br.-d, 2H), 4.22–4.06 (m, 5H), 3.57 (s, 3H), 3.39–3.31 (br.-t, 2H), 2.97–2.93 (m, 2H), 2.42 (s, 3H), 1.87–1.84 (br.-d, 2H), 1.49 (t, 3H, J=7.0 Hz), 1.47 (t, 3H, J=7.0 Hz), 1.32 (d, 6H, J=6.0 Hz). (as the free base)

IR (KBr tab.)(cm⁻¹): 1699, 1659, 1634, 1542, 1518.

Melting Point (ethanol-ethyl acetate-ether): 170–172° C.

EXAMPLE 21

3-[1-(2-Cyclohexylamino-6,7-diethoxy-4-quinazolinyl)-4-piperidinyl]-1,2,3,4-tetrahydro-1,6-dimethyl-2,4-dioxoquinazoline hydrochloride (Compound 21)

The same procedure as in Example 10 was repeated, except that cyclohexylamine was used in place of morpholine, to give Compound 21 as white crystals.

¹H-NMR (CDCl₃) δ: 8.01 (d, 1H, J=1.5 Hz), 7.49 (dd, 1H, J=8.5, 1.5 Hz), 7.09 (d, 1H, J=8.5 Hz), 7.09 (s, 1H), 6.91 (s, 1H), 5.40–5.20 (m, 1H), 4.37–4.23 (br.-d, 2H), 4.19 (q, 2H, J=7.0 Hz), 4.10 (q, 2H, J=7.0 Hz), 4.00–3.80 (m, 1H), 3.58 (s, 3H), 3.22–3.13 (br.-t, 2H), 3.05–2.97 (m, 2H), 2.42 (s, 3H), 2.06–2.03 (m, 2H), 1.85–1.75 (m, 4H), 1.50 (t, 3H, J=7.0 Hz), 1.48 (t, 3H, J=7.0 Hz), 1.38–1.27 (m, 6H). (as the free base)

IR (KBr tab.)(cm⁻¹): 1702, 1654, 1635, 1599, 1542.

Melting Point (ethyl acetate): 170–173° C.

EXAMPLE 22

3-[1-(2-Cyclooctylamino-6,7-diethoxy-4-quinazolinyl)-4-piperidinyl]-1,2,3,4-tetrahydro-1,6-dimethyl-2,4-dioxoquinazoline hydrochloride (Compound 22)

The same procedure as in Example 10 was repeated, except that cyclooctylamine was used in place of morpholine, to give Compound 22 as white crystals.

¹H-NMR (CDCl₃) δ: 8.15 (br.-d, 1H, NH), 8.01 (d, 1H, J=1.5 Hz), 7.50 (dd, 1H, J=8.5, 1.5 Hz), 7.10 (d, 1H, J=8.5 Hz), 7.08 (s, 1H), 6.92 (s, 1H), 5.40–5.20 (m, 1H), 4.69–4.64 (br.-d, 2H), 4.20 (q, 2H, J=7.0 Hz), 4.07 (q, 2H, J=7.0 Hz), 4.20–4.00 (m, 1H), 3.58 (s, 3H), 3.40–3.31 (br.-t, 2H), 3.02–2.94 (m, 2H), 2.43 (s, 3H), 2.00–1.50 (m, 16H), 1.50 (t, 3H, J=7.0 Hz), 1.47 (t, 3H, J=7.0 Hz). (as the hydrochloride)

IR (KBr tab.)(cm⁻¹): 1704, 1699, 1657, 1636, 1359.

Melting Point (ether): 231–234° C.

EXAMPLE 23

3-[1-(6,7-Methylenedioxy-2-morpholino-4-quinazolinyl)-4-piperidinyl]-1,2,3,4-tetrahydro-1,6-dimethyl-2,4-dioxoquinazoline hydrochloride (Compound 23)

The same procedure as in Example 10 was repeated, except that 3-[1-(2-chloro-6,7-methylenedioxy-4-quinazolinyl)-4-piperidinyl]-1,2,3,4-tetrahydro-1,6-dimethyl-2,4-dioxoquinazoline (Compound c) obtained in Reference Example 3 was used in place of Compound b, to give Compound 23 as white crystals.

¹H-NMR (CDCl₃) δ: 8.02 (d, 1H, J=2.0 Hz), 7.49 (dd, 1H, J=8.6, 2.0 Hz), 7.09 (s, 1H), 7.09 (d, 1H, J=8.6 Hz), 6.90 (s, 1H), 6.01 (s, 2H), 5.30–5.10 (m, 1H), 4.20–4.10 (br.-d, 2H), 3.90–3.70 (m, 8H), 3.58 (s, 3H), 3.10–2.95 (m, 4H), 2.42 (s, 3H), 1.86–1.75 (br.-d, 2H). (as the free base)

IR (KBr tab.)(cm⁻¹): 1702, 1654, 1649, 1510.

Melting Point (ethanol-ether): 278–280° C.

EXAMPLE 24

3-[1-(2-Morpholino-6,7-dipropoxy-4-quinazolinyl)-4-piperidinyl]-1,2,3,4-tetrahydro-1,6-dimethyl-2,4-dioxoquinazoline hydrochloride (Compound 24)

The same procedure as in Example 10 was repeated, except that 3-[1-(2-chloro-6,7-dipropoxy-4-quinazolinyl)-4-piperidinyl]-1,2,3,4-tetrahydro-1,6-dimethyl-2,4-dioxoquinazoline (Compound d) obtained in Reference Example 4 was used in place of Compound b, to give Compound 24 as white crystals.

¹H-NMR (CDCl₃) δ: 8.02 (d, 1H, J=1.5 Hz), 7.48 (dd, 1H, J=8.3, 1.5 Hz), 7.10 (s, 1H), 7.08 (d, 1H, J=8.3 Hz), 6.91 (s, 1H), 5.30–5.25 (m, 1H), 4.30–4.20 (br.-d, 2H), 4.07 (t, 2H, J=6.5 Hz), 4.00 (t, 2H, J=6.5 Hz), 3.90–3.81 (m, 8H), 3.58 (s, 3H), 3.09–2.99 (m, 4H), 2.42 (s, 3H), 1.94–1.80 (m, 6H), 1.07 (t, 6H, J=6.5 Hz). (as the free base)

IR (KBr tab.)(cm⁻¹): 1704, 1656, 1631, 1596, 1511.

Melting Point (ethanol-ether-hexane): 160–163° C.

EXAMPLE 25

3-[1-(6,7-Diisopropoxy-2-morpholino-4-quinazolinyl)-4-piperidinyl]-1,2,3,4-tetrahydro-1,6-dimethyl-2,4-dioxoquinazoline hydrochloride (Compound 25)

The same procedure as in Example 10 was repeated, except that 3-[1-(2-chloro-6,7-diisopropoxy-4-quinazolinyl)-4-piperidinyl]-1,2,3,4-tetrahydro-1,6-dimethyl-2,4-dioxoquinazoline (Compound e) obtained in Reference Example 5 was used in place of Compound b, to give Compound 25 as white crystals.

¹H-NMR (CDCl₃) δ: 8.02 (d, 1H, J=1.5 Hz), 7.58 (dd, 1H, J=8.5, 1.5 Hz), 7.22 (s, 1H), 7.08 (d, 1H, J=8.5 Hz), 6.92 (s, 1H), 5.30–5.10 (m, 1H), 4.69 (sept, 1H, J=6.0 Hz), 4.41 (sept, 1H, J=6.0 Hz), 4.29–4.26 (br.-d, 2H), 3.90–3.75 (m, 8H), 3.58 (s, 3H), 3.09–2.98 (m, 4H), 2.42 (s, 3H), 1.82–1.79 (br.-d, 2H), 1.42 (d, 3H, J=6.0 Hz), 1.34 (d, 3H, J=6.0 Hz). (as the free base)

IR (KBr tab.)(cm⁻¹): 1704, 1652, 1543, 1510.

Melting Point (ethanol-ethyl acetate-ether): 189–192° C.

EXAMPLE 26

3-[1-(7-Benzyloxy-6-methoxy-2-morpholino-4-quinazolinyl)-4-piperidinyl]-1,2,3,4-tetrahydro-1,6-dimethyl-2,4-dioxoquinazoline hydrochloride (Compound 26)

The same procedure as in Example 10 was repeated, except that 3-[1-(7-benzyloxy-2-chloro-6-methoxy-4-quinazolinyl)-4-piperidinyl]-1,2,3,4-tetrahydro-1,6-dimethyl-2,4-dioxoquinazoline (Compound f) obtained in Reference Example 6 was used in place of Compound b, to give Compound 26 as white crystals.

¹H-NMR (CDCl₃) δ: 8.02 (d, 1H, J=1.5 Hz), 7.51–7.26 (m, 6H), 7.10 (s, 1H), 7.08 (d, 1H, J=8.5 Hz), 6.99 (s, 1H), 5.40–5.20 (m, 3H), 4.30–4.20 (br.-d, 2H), 3.92 (s, 3H), 3.90–3.60 (m, 8H), 3.58 (s, 3H), 3.21–2.95 (m, 4H), 2.42 (s, 3H), 1.83–1.75 (br.-d, 2H). (as the free base)

IR (KBr tab.)(cm$^{-1}$): 1704, 1657, 1649, 1540, 1273.
Melting Point (ether): 176–178° C.

EXAMPLE 27

3-[1-(6,7-Dimethoxy-2-morpholino-4-quinazolinyl)-4-piperidinyl]methyl-1,2,3,4-tetrahydro-1,6-dimethyl-2,4-dioxoquinazoline (Compound 27)

The same procedure as in Example 1 was repeated, except that 300 mg (0.59 mmol) of 3-[1-(2-chloro-6,7-dimethoxy-4-quinazolinyl)-4-piperidinyl]methyl-1,2,3,4-tetrahydro-1,6-dimethyl-2,4-dioxoquinazoline (Compound h) obtained in Reference Example 9 was used in place of Compound a, and N-methylpyrrolidinone was used as the solvent in place of dimethylformamide, to give 250 mg (yield: 76%) of Compound 27 as white crystals.

$^1$H-NMR (CDCl$_3$) δ: 8.02 (s, 1H), 7.48 (d, 1H, J=8.4 Hz), 7.12 (d, 1H, J=8.4 Hz), 6.98 (s, 1H), 6.92 (br.-s, 1H), 4.16–4.04 (br.-d, 4H), 3.97 (s, 3H), 3.92 (s, 3H), 3.80 (br.-s, 8H), 3.65 (s, 3H), 3.07–2.98 (m, 2H), 2.42 (s, 3H), 2.28–2.10 (m, 1H), 1.83–1.59 (m, 4H).

Melting Point (methanol-water): 255–256° C.

EXAMPLE 28

3-{1-[2-Bis(2-hydroxyethyl)amino-6,7-dimethoxy-4-quinazolinyl]-4-piperidinyl}methyl-1,2,3,4-tetrahydro-1,6-dimethyl-2,4-dioxoquinazoline (Compound 28)

The same procedure as in Example 27 was repeated, except that diethanolamine was used in place of morpholine, to give Compound 28 as white crystals.

$^1$H-NMR (CDCl$_3$) δ: 8.02 (s, 1H), 7.50 (d, 1H, J=8.6 Hz), 7.12 (d, 1H, J=8.6 Hz), 6.96 (s, 1H), 6.87 (br.-s, 1H), 4.17–4.04 (br.-d, 4H), 3.98 (s, 3H), 3.91 (s, 3H), 3.91–3.82 (m, 8H), 3.60 (s, 3H), 3.04–2.95 (br.-t, 2H), 2.42 (s, 3H), 2.31–2.13 (m, 1H), 1.88–1.77 (br.-d, 2H), 1.71–1.57 (m, 2H).

Melting Point (methanol-water): 223–224° C.

EXAMPLE 29

3-{2-[1-(6,7-Dimethoxy-2-morpholino-4-quinazolinyl)-4-piperidinyl]ethyl}-1,2,3,4-tetrahydro-6-methyl-2,4-dioxoquinazoline (Compound 29)

Ethyl chlorocarbonate (10 ml) was added to 540 mg (1.01 mmol) of 4-[2-(2-amino-5-methylbenzoylamino)ethyl]-1-(6,7-dimethoxy-2-morpholino-4-quinazolinyl)piperidine (Compound 1) obtained in Reference Example 13, and the mixture was heated under reflux for 10 hours. After cooling to room temperature, the solvent was evaporated under reduced pressure, followed by addition of hexane and ether to the residue. The precipitated crystals were collected by filtration to give 430 mg of crude 4-[2-(2-ethoxycarbonylamino-5-methylbenzoylamino)ethyl]-1-(6,7-dimethoxy-2-morpholino-4-quinazolinyl)piperidine, which was then dissolved in 10 ml of ethanol. To the solution was added 210 mg of potassium hydroxide, and the mixture was heated under reflux for one hour. After evaporation of the solvent under reduced pressure, water was added to the residue, followed by extraction with chloroform. The organic layer was washed and dried, and the solvent was evaporated to give 360 mg (overall yield: 64%) of Compound 29 as white crystals.

$^1$H-NMR (CDCl$_3$) δ: 8.95 (br.-s, 1H, NH), 7.92 (s, 1H), 7.42 (d, 1H, J=8.3 Hz), 6.99–6.96 (m, 3H), 4.20–4.12 (m, 4H), 4.00 (s, 3H), 3.92 (s, 3H), 3.80 (br.-s, 8H), 3.14–3.00 (br.-t, 2H), 2.40 (s, 3H), 2.01–1.97 (br.-d, 2H), 1.74–1.54 (m, 5H).

Melting Point (methanol-water): 185–188° C.

EXAMPLE 30

3-{2-[1-(6,7-Dimethoxy-2-morpholino-4-quinazolinyl)-4-piperidinyl]ethyl}-1,2,3,4-tetrahydro-1,6-dimethyl-2,4-dioxoquinazoline (Compound 30)

In 5 ml of dimethylformamide was suspended 350 mg (0.7 mmol) of Compound 29 obtained in Example 29, and 42 mg (1.05 mmol) of 60% sodium hydride and 0.1 ml (1.54 mmol) of methyl iodide were added to the suspension. The mixture was stirred at room temperature for one hour, and then a saturated aqueous solution of ammonium chloride was added thereto to stop the reaction. After extraction with ethyl acetate, the organic layer was washed and dried. The solvent was evaporated under reduced pressure, and the resulting crude crystals were washed with a solvent mixture of ethanol and ether to give 190 mg (yield: 48%) of Compound 30 as white crystals.

$^1$H-NMR (CDCl$_3$) δ: 8.02 (s, 1H), 7.50 (d, 1H, J=8.6 Hz), 7.11 (d, 1H, J=8.6 Hz), 6.98 (s, 1H), 6.95 (br.-s, 1H), 4.18–4.06 (m, 4H), 3.99 (s, 3H), 3.92 (s, 3H), 3.81 (br.-s, 8H), 3.59 (s, 3H), 3.12–2.95 (m, 2H), 2.42 (s, 3H), 2.05–1.91 (m, 2H), 1.80–1.42 (m, 5H).

Melting Point (ethanol-ether): 138° C.

EXAMPLE 31

3-{2-{1-[2-Bis(2-hydroxyethyl)amino-6,7-dimethoxy-4-quinazolinyl]-4-piperidinyl}ethyl}-1,2,3,4-tetrahydro-6-methyl-2,4-dioxoquinazoline (Compound 31)

The same procedure as in Example 29 was repeated, except that 4-[2-(2-amino-5-methylbenzoylamino)ethyl]-1-[2-bis(2-hydroxyethyl)amino-6,7-dimethoxy-4-quinazolinyl] piperidine (Compound j) obtained in Reference Example 14 was used in place of Compound i, to give Compound 31 as white crystals.

$^1$H-NMR (CDCl$_3$) δ: 7.91 (s, 1H), 7.40 (d, 1H, J=8.6 Hz), 6.99–6.95 (m, 3H), 4.16–4.11 (m, 4H), 3.96 (s, 3H), 3.91 (s, 3H), 3.94–3.84 (m, 8H), 3.09–3.00 (br.-t, 2H), 2.40 (s, 3H), 2.02–1.97 (br.-d, 2H), 1.80–1.49 (m, 5H).

Melting Point (methanol-water): 167–169° C.

EXAMPLE 32

3-[1-(6,7-Diethoxy-2-morpholino-4-quinazolinyl)-4-piperidinyl]-1,2,3,4-tetrahydro-2,4-dioxoquinazoline (Compound 32)

The same procedure as in Example 10, Step 1 was repeated, except that 3-[1-(2-chloro-6,7-diethoxy-4-quinazolinyl)-4-piperidinyl]-1,2,3,4-tetrahydro-2,4-dioxoquinazoline (Compound p) obtained in Reference Example 15 was used in place of Compound b, to give Compound 32 as white crystals.

$^1$H-NMR (CDCl$_3$) δ: 9.67 (br.-s, 1H, NH), 8.13 (dd, 1H, J=6.9, 1.8 Hz), 7.59 (ddd, 1H, J=6.9, 6.9, 1.8 Hz), 7.23 (ddd, 1H, J=6.9, 6.9, 1.8 Hz), 7.11 (s, 1H), 7.00 (dd, 1H, J=6.9, 1.8 Hz), 6.95 (br.-s, 1H), 5.30–5.15 (m, 1H), 4.32–4.27 (br.-d, 2H), 4.21 (q, 2H, J=7.0 Hz), 4.11 (q, 2H, J=7.0 Hz), 3.83–3.77 (m, 8H), 3.19–2.98 (m, 4H), 1.84–1.80 (br.-d, 2H), 1.51 (t, 3H, J=7.0 Hz), 1.46 (t, 3H, J=7.0 Hz).

IR (KBr tab.)(cm$^{-1}$): 1705, 1656, 1560, 1441, 1234, 764.

Melting Point (ether): 193–194° C.

EXAMPLE 33

3-[1-(6,7-Diethoxy-2-morpholino-4-quinazolinyl)-4-piperidinyl]-1,2,3,4-tetrahydro-1-methyl-2,4-dioxoquinazoline (Compound 33)

The same procedure as in Example 10, Step 1 was repeated, except that 3-[1-(2-chloro-6,7-diethoxy-4-quinazolinyl)-4-piperidinyl]-1,2,3,4-tetrahydro-1-methyl-2,4-dioxoquinazoline (Compound q) obtained in Reference Example 16 was used in place of Compound b, to give Compound 33 as white crystals.

$^1$H-NMR (CDCl$_3$) δ: 8.30 (dd, 1H, J=7.9, 1.0 Hz), 7.68 (ddd, 1H, J=7.9, 7.9, 1.0 Hz), 7.26 (ddd, 1H, J=7.9, 7.9, 1.0 Hz), 7.19 (dd, 1H, J=7.9, 1.0 Hz), 7.11 (s, 1H), 6.92 (br.-s, 1H), 5.30–5.15 (m, 1H), 4.30–4.25 (br.-d, 2H), 4.20 (q, 2H, J=7.0 Hz), 4.12 (q, 2H, J=7.0 Hz), 3.84–3.81 (m, 8H), 3.60 (s, 3H), 3.15–2.96 (m, 4H), 1.82–1.79 (br.-d, 2H), 1.51 (t, 3H, J=7.0 Hz), 1.49 (t, 3H, J=7.0 Hz).

IR (KBr tab.)(cm$^{-1}$): 1702, 1658, 1562, 1510, 1238.

Melting Point (ether): 238–241° C.

EXAMPLE 34

3-[1-(6,7-Diethoxy-2-morpholino-4-quinazolinyl)-4-piperidinyl]-1,2,3,4-tetrahydro-6-methyl-2,4-dioxoquinazoline (Compound 34)

The same procedure as in Example 10, Step 1 was repeated, except that 3-[1-(2-chloro-6,7-diethoxy-4-quinazolinyl)-4-piperidinyl]-1,2,3,4-tetrahydro-6-methyl-2,4-dioxoquinazoline (Compound r) obtained in Reference Example 17 was used in place of Compound b, to give Compound 34 as white crystals.

$^1$H-NMR (CDCl$_3$) δ: 9.05 (br.-s, 1H, NH), 7.92 (d, 1H, J=2.0 Hz), 7.40 (dd, 1H, J=8.0, 2.0 Hz), 7.10 (s, 1H), 6.92 (br.-s, 1H), 6.90 (d, 1H, J=8.0 Hz), 5.25–5.15 (m, 1H), 4.30–4.15 (m, 4H), 4.10 (q, 2H, J=7.0 Hz), 3.83–3.80 (m, 8H), 3.13–2.99 (m, 4H), 2.40 (s, 3H), 1.83–1.80 (br.-d, 2H), 1.52 (t, 3H, J=7.0 Hz), 1.47 (t, 3H, J=7.0 Hz).

IR (KBr tab.)(cm$^{-1}$): 1710, 1659, 1560, 1433.

Melting Point (ether): 229–232° C.

EXAMPLE 35

3-[1-(6,7-Diethoxy-2-morpholino-4-quinazolinyl)-4-piperidinyl]-1-ethyl-1,2,3,4-tetrahydro-6-methyl-2,4-dioxoquinazoline (Compound 35)

The same procedure as in Example 10, Step 1 was repeated, except that 3-[1-(2-chloro-6,7-diethoxy-4-quinazolinyl)-4-piperidinyl]-1-ethyl-1,2,3,4-tetrahydro-6-methyl-2,4-dioxoquinazoline (Compound s) obtained in Reference Example 18 was used in place of Compound b, to give Compound 35 as white crystals.

$^1$H-NMR (CDCl$_3$) δ: 8.02 (d, 1H, J=2.0 Hz), 7.48 (dd, 1H, J=8.3, 2.0 Hz), 7.10 (s, 1H), 7.09 (d, 1H, J=8.3 Hz), 6.92 (br.-s, 1H), 5.30–5.10 (m, 1H), 4.40–4.20 (m, 4H), 4.16 (q, 2H, J=7.0 Hz), 4.12 (q, 2H, J=7.0 Hz), 3.95–3.81 (m, 8H), 3.20–2.96 (m, 4H), 2.41 (s, 3H), 1.82–1.79 (br.-d, 2H), 1.51 (t, 3H, J=7.0 Hz), 1.49 (t, 3H, J=7.0 Hz), 1.35 (t, 3H, J=7.0 Hz).

IR (KBr tab.)(cm$^{-1}$): 1707, 1653, 1542, 1457.

Melting Point (ether): 227–230° C.

EXAMPLE 36

3-[1-(6,7-Diethoxy-2-morpholino-4-quinazolinyl)-4-piperidinyl]-1,2,3,4-tetrahydro-6-methyl-2,4-dioxo-1-propylquinazoline (Compound 36)

The same procedure as in Example 10, Step 1 was repeated, except that 3-[1-(2-chloro-6,7-diethoxy-4-quinazolinyl)-4-piperidinyl]-1,2,3,4-tetrahydro-6-methyl-2,4-dioxo-1-propylquinazoline (Compound t) obtained in Reference Example 19 was used in place of Compound b, to give Compound 36 as white crystals.

$^1$H-NMR (CDCl$_3$) δ: 8.02 (d, 1H, J=2.0 Hz), 7.46 (dd, 1H, J=8.3, 2.0 Hz), 7.10 (s, 1H), 7.06 (d, 1H, J=8.3 Hz), 6.92 (br.-s, 1H), 5.25–5.10 (m, 1H), 4.22–4.19 (br.-d, 2H), 4.17 (q, 2H, J=7.0 Hz), 4.12 (q, 2H, J=7.0 Hz), 4.08–4.02 (br.-t, 2H), 3.90–3.81 (m, 8H), 3.07–2.99 (m, 4H), 2.41 (s, 3H), 1.81–1.78 (br.-d, 2H), 1.51 (t, 3H, J=7.0 Hz), 1.49 (t, 3H, J=7.0 Hz), 1.04 (t, 3H, J=7.0 Hz).

IR (KBr tab.)(cm$^{-1}$): 1701, 1658, 1573, 1509, 1460, 1238.

Melting Point (ether): 162–163° C.

EXAMPLE 37

3-[1-(6,7-Diethoxy-2-morpholino-4-quinazolinyl)-4-piperidinyl]-1,2,3,4-tetrahydro-5-methyl-2,4-dioxoquinazoline (Compound 37)

The same procedure as in Example 10, Step 1 was repeated, except that 3-[1-(2-chloro-6,7-diethoxy-4-quinazolinyl)-4-piperidinyl]-1,2,3,4-tetrahydro-5-methyl-2,4-dioxoquinazoline (Compound u) obtained in Reference Example 20 was used in place of Compound b, to give Compound 37 as white crystals.

$^1$H-NMR (CDCl$_3$) δ: 9.43 (br.-s, 1H, NH), 7.40 (dd, 1H, J=7.9, 7.9 Hz), 7.11 (s, 1H), 6.99 (d, 1H, J=7.9 Hz), 6.95 (br.-s, 1H), 6.82 (d, 1H, J=7.9 Hz), 5.25–5.10 (m, 1H), 4.27–4.15 (br.-d, 2H), 4.21 (q, 2H, J=7.0 Hz), 4.11 (q, 2H, J=7.0 Hz), 3.83–3.71 (m, 8H), 3.18–2.97 (m, 4H), 2.79 (s, 3H), 1.83–1.79 (br.-d, 2H), 1.52 (t, 3H, J=7.0 Hz), 1.47 (t, 3H, J=7.0 Hz).

IR (KBr tab.)(cm$^{-1}$): 1710, 1653, 1469, 1433, 1233.

Melting Point (ether): 261–263° C.

EXAMPLE 38

3-[1-(6,7-Diethoxy-2-morpholino-4-quinazolinyl)-4-piperidinyl]-1,2,3,4-tetrahydro-1,5-dimethyl-2,4-dioxoquinazoline (Compound 38)

The same procedure as in Example 10, Step 1 was repeated, except that 3-[1-(2-chloro-6,7-diethoxy-4-quinazolinyl)-4-piperidinyl]-1,2,3,4-tetrahydro-1,5-dimethyl-2,4-dioxoquinazoline (Compound v) obtained in Reference Example 21 was used in place of Compound b, to give Compound 38 as white crystals.

$^1$H-NMR (CDCl$_3$) δ: 7.51 (dd, 1H, J=7.6, 7.6 Hz), 7.11 (s, 1H), 7.05 (d, 2H, J=7.6 Hz), 6.93 (br.-s, 1H), 5.25–5.10 (m, 1H), 4.28–4.24 (br.-d, 2H), 4.20 (q, 2H, J=7.0 Hz), 4.13 (q, 2H, J=7.0 Hz), 3.84–3.80 (m, 8H), 3.58 (s, 3H), 3.14–2.98 (m, 4H), 2.82 (s, 3H), 1.81–1.78 (br.-d, 2H), 1.51 (t, 3H, J=7.0 Hz), 1.49 (t, 3H, J=7.0 Hz).

IR (KBr tab.)(cm$^{-1}$): 1699, 1655, 1560, 1236.

Melting Point (ether): 170–172° C.

EXAMPLE 39

3-[1-(6,7-Diethoxy-2-morpholino-4-quinazolinyl)-4-piperidinyl]-1,2,3,4-tetrahydro-8-methyl-2,4-dioxoquinazoline (Compound 39)

The same procedure as in Example 10, Step 1 was repeated, except that 3-[1-(2-chloro-6,7-diethoxy-4-quinazolinyl)-4-piperidinyl]-1,2,3,4-tetrahydro-8-methyl-2,4-dioxoquinazoline (Compound w) obtained in Reference Example 22 was used in place of Compound b, to give Compound 39 as white crystals.

$^1$H-NMR (CDCl$_3$) δ: 9.12 (br.-s, 1H, NH), 8.00 (d, 1H, J=7.6 Hz), 7.40 (d, 1H, J=7.6 Hz), 7.13 (dd, 1H, J=7.6, 7.6 Hz), 7.10 (s, 1H), 6.95 (br.-s, 1H), 5.30–5.15 (m, 1H), 4.32–4.28 (br.-d, 2H), 4.22 (q, 2H, J=7.0 Hz), 4.10 (q, 2H, J=7.0 Hz), 3.83–3.78 (m, 8H), 3.18–2.99 (m, 4H), 2.35 (s, 3H), 1.84–1.80 (br.-d, 2H), 1.52 (t, 3H, J=7.0 Hz), 1.46 (t, 3H, J=7.0 Hz).

IR (KBr tab.)(cm$^{-1}$): 1720, 1659, 1649, 1510, 1235, 756.

Melting Point (ether): 222–226° C.

EXAMPLE 40

3-[1-(6,7-Diethoxy-2-morpholino-4-quinazolinyl)-4-piperidinyl]-1,2,3,4-tetrahydro-1,8-dimethyl-2,4-dioxoquinazoline (Compound 40)

The same procedure as in Example 10, Step 1 was repeated, except that 3-[1-(2-chloro-6,7-diethoxy-4-quinazolinyl)-4-piperidinyl]-1,2,3,4-tetrahydro-1,8-dimethyl-2,4-dioxoquinazoline (Compound x) obtained in Reference Example 23 was used in place of Compound b, to give Compound 40 as white crystals.

$^1$H-NMR (CDCl$_3$) δ: 8.06 (d, 1H, J=7.0 Hz), 7.45 (d, 1H, J=7.0 Hz), 7.18 (dd, 1H, J=7.0, 7.0 Hz), 7.10 (s, 1H), 6.93 (br.-s, 1H), 5.20–5.00 (m, 1H), 4.30–4.20 (br.-d, 2H), 4.20 (q, 2H, J=7.0 Hz), 4.12 (q, 2H, J=7.0 Hz), 3.85–3.80 (m, 8H), 3.67 (s, 3H), 3.09–2.97 (m, 4H), 2.61 (s, 3H), 1.83–1.80 (br.-d, 2H), 1.51 (t, 3H, J=7.0 Hz), 1.49 (t, 3H, J=7.0 Hz).

IR (KBr tab.)(cm$^{-1}$): 1722, 1675, 1580, 1466, 1257.

Melting Point (ethyl acetate-ether): 141–143° C.

EXAMPLE 41

6-Chloro-3-[1-(6,7-diethoxy-2-morpholino-4-quinazolinyl)-4-piperidinyl]-1,2,3,4-tetrahydro-2,4-dioxoquinazoline (Compound 41)

The same procedure as in Example 10, Step 1 was repeated, except that 6-chloro-3-[1-(2-chloro-6,7-diethoxy-4-quinazolinyl)-4-piperidinyl]-1,2,3,4-tetrahydro-2,4-dioxoquinazoline (Compound y) obtained in Reference Example 24 was used in place of Compound b, to give Compound 41 as white crystals.

$^1$H-NMR (CDCl$_3$) δ: 10.00 (br.-s, 1H, NH), 8.09 (d, 1H, J=2.0 Hz), 7.55 (dd, 1H, J=8.5, 2.0 Hz), 7.10 (s, 1H), 6.97 (s, 1H), 6.94 (d, 1H, J=8.5 Hz), 5.30–5.15 (m, 1H), 4.32–4.27 (br.-d, 2H), 4.21 (q, 2H, J=7.0 Hz), 4.11 (q, 2H, J=7.0 Hz), 3.82–3.78 (m, 8H), 3.19–2.99 (m, 4H), 1.81–1.77 (br.-d, 2H), 1.52 (t, 3H, J=7.0 Hz), 1.48 (t, 3H, J=7.0 Hz).

IR (KBr tab.)(cm$^{-1}$): 1715, 1658, 1562, 1471, 1342, 1235.

Melting Point (ether): 126–129° C.

EXAMPLE 42

6-Chloro-3-[1-(6,7-diethoxy-2-morpholino-4-quinazolinyl)-4-piperidinyl]-1,2,3,4-tetrahydro-1-methyl-2,4-dioxoquinazoline (Compound 42)

The same procedure as in Example 10, Step 1 was repeated, except that 6-chloro-3-[1-(2-chloro-6,7-diethoxy-4-quinazolinyl)-4-piperidinyl]-1,2,3,4-tetrahydro-1-methyl-2,4-dioxoquinazoline (Compound z) obtained in Reference Example 25 was used in place of Compound b, to give Compound 42 as white crystals.

$^1$H-NMR (CDCl$_3$) δ: 8.18 (d, 1H, J=2.6 Hz), 7.62 (dd, 1H, J=8.9, 2.6 Hz), 7.14 (d, 1H, J=8.9 Hz), 7.09 (s, 1H), 6.93 (br.-s, 1H), 5.30–5.10 (m, 1H), 4.30–4.20 (br.-d, 2H), 4.19 (q, 2H, J=7.0 Hz), 4.12 (q, 2H, J=7.0 Hz), 3.84–3.80 (m, 8H), 3.58 (s, 3H), 3.10–2.93 (m, 4H), 1.81–1.77 (br.-d, 2H), 1.52 (t, 3H, J=7.0 Hz), 1.49 (t, 3H, J=7.0 Hz).

IR (KBr tab.)(cm$^{-1}$): 1705, 1699, 1667, 1543, 1422, 1231.

Melting Point (ether): 213–215° C.

EXAMPLE 43

6-Bromo-3-[1-(6,7-diethoxy-2-morpholino-4-quinazolinyl)-4-piperidinyl]-1,2,3,4-tetrahydro-1-methyl-2,4-dioxoquinazoline (Compound 43)

The same procedure as in Example 10, Step 1 was repeated, except that 6-bromo-3-[1-(2-chloro-6,7-diethoxy-4-quinazolinyl)-4-piperidinyl]-1,2,3,4-tetrahydro-1-methyl-2,4-dioxoquinazoline (Compound aa) obtained in Reference Example 26 was used in place of Compound b, to give Compound 43 as white crystals.

$^1$H-NMR (CDCl$_3$) δ: 8.33 (d, 1H, J=2.3 Hz), 7.75 (dd, 1H, J=8.9, 2.3 Hz), 7.09 (s, 1H), 7.07 (d, 1H, J=8.9 Hz), 6.93 (br.-s, 1H), 5.30–5.15 (m, 1H), 4.30–4.20 (br.-d, 2H), 4.19 (q, 2H, J=7.0 Hz), 4.12 (q, 2H, J=7.0 Hz), 3.90–3.80 (m, 8H), 3.58 (s, 3H), 3.10–2.96 (m, 4H), 1.81–1.77 (br.-d, 2H), 1.52 (t, 3H, J=7.0 Hz), 1.49 (t, 3H, J=7.0 Hz).

IR (KBr tab.)(cm$^{-1}$): 1726, 1682, 1462, 1256.

Melting Point (ether-hexane): 206–207° C.

EXAMPLE 44

3-[1-(6,7-Diethoxy-2-morpholino-4-quinazolinyl)-4-piperidinyl]-1,2,3,4-tetrahydro-6-nitro-2,4-dioxoquinazoline (Compound 44)

The same procedure as in Example 10, Step 1 was repeated, except that 3-[1-(2-chloro-6,7-diethoxy-4-quinazolinyl)-4-piperidinyl]-1,2,3,4-tetrahydro-6-nitro-2,4-dioxoquinazoline (Compound bb) obtained in Reference Example 27 was used in place of Compound b, to give Compound 44 as white crystals.

$^1$H-NMR (CDCl$_3$) δ: 9.01 (d, 1H, J=2.0 Hz), 8.48 (dd, 1H, J=8.5, 2.0 Hz), 7.09 (s, 1H), 7.03 (d, 1H, J=8.5 Hz), 7.00 (s, 1H), 5.30–5.15 (m, 1H), 4.34–4.30 (br.-d, 2H), 4.22 (q, 2H, J=7.0 Hz), 4.12 (q, 2H, J=7.0 Hz), 3.81–3.77 (m, 8H), 3.23–3.14 (br.-t, 2H), 3.01–2.97 (m, 2H), 1.81–1.78 (br.-d, 2H), 1.52 (t, 3H, J=7.0 Hz), 1.48 (t, 3H, J=7.0 Hz).

IR (KBr tab.)(cm$^{-1}$): 1719, 1659, 1648, 1561, 1337, 1233.

Melting Point (ether): 154–156° C.

EXAMPLE 45

3-[1-(6,7-Diethoxy-2-morpholino-4-quinazolinyl)-4-piperidinyl]-1,2,3,4-tetrahydro-1-methyl-6-nitro-2,4-dioxoquinazoline (Compound 45)

The same procedure as in Example 10, Step 1 was repeated, except that 3-[1-(2-chloro-6,7-diethoxy-4-quinazolinyl)-4-piperidinyl]-1,2,3,4-tetrahydro-1-methyl-6-nitro-2,4-dioxoquinazoline (Compound cc) obtained in Reference Example 28 was used in place of Compound b, to give Compound 45 as white crystals.

$^1$H-NMR (CDCl$_3$) δ: 9.09 (d, 1H, J=2.6 Hz), 8.51 (dd, 1H, J=9.2, 2.6 Hz), 7.31 (d, 1H, J=9.2 Hz), 7.09 (s, 1H), 6.94 (br.-s, 1H), 5.30–5.15 (m, 1H), 4.30–4.15 (br.-d, 2H), 4.18 (q, 2H, J=7.0 Hz), 4.12 (q, 2H, J=7.0 Hz), 3.90–3.80 (m, 8H), 3.67 (s, 3H), 3.10–2.96 (m, 4H), 1.83–1.79 (br.-d, 2H), 1.52 (t, 3H, J=7.0 Hz), 1.49 (t, 3H, J=7.0 Hz).

IR (KBr tab.)(cm$^{-1}$): 1720, 1672, 1331, 1234.

Melting Point (ether): 158–160° C.

EXAMPLE 46

6-Acetyl-3-[1-(6,7-diethoxy-2-morpholino-4-quinazolinyl)-4-piperidinyl]-1,2,3,4-tetrahydro-1-methyl-2,4-dioxoquinazoline (Compound 46)

The same procedure as in Example 10, Step 1 was repeated, except that 6-acetyl-3-[1-(2-chloro-6,7-diethoxy-4-quinazolinyl)-4-piperidinyl]-1,2,3,4-tetrahydro-1-methyl-2,4-dioxoquinazoline (Compound dd) obtained in Reference Example 29 was used in place of Compound b, to give Compound 46 as white crystals.

$^1$H-NMR (CDCl$_3$) δ: 8.77 (d, 1H, J=2.0 Hz), 8.31 (dd, 1H, J=8.9, 2.0 Hz), 7.27 (d, 1H, J=8.9 Hz), 7.10 (s, 1H), 6.93 (br.-s, 1H), 5.30–5.10 (m, 1H), 4.30–4.20 (br.-d, 2H), 4.21 (q, 2H, J=7.0 Hz), 4.13 (q, 2H, J=7.0 Hz), 3.84–3.82 (m, 8H), 3.64 (s, 3H), 3.12–2.98 (m, 4H), 2.67 (s, 3H), 1.83–1.79 (br.-d, 2H), 1.52 (t, 3H, J=7.0 Hz), 1.49 (t, 3H, J=7.0 Hz).

IR (KBr tab.)(cm$^{-1}$): 1707, 1685, 1649, 1510.

Melting Point (ether): 153–154° C.

EXAMPLE 47

3-[1-(6-Ethoxy-7-hydroxy-2-morpholino-4-quinazolinyl)-4-piperidinyl]-1,2,3,4-tetrahydro-1,6-dimethyl-2,4-dioxoquinazoline (Compound 47)

In 10 ml of DMF was suspended 1.19 g (30.0 mmol) of 60% sodium hydride, and 3.07 ml (30.0 mmol) of thiophenol in 20 ml of DMF was dropwised under ice-cooling. After the mixture was stirred at ice-cooling for 10 minutes, 5.74 g (10.0 mmol) of Compound 10 obtained in Example 10 in DMF (50 ml) was added at ice-cooling, then the reaction mixture was stirred at 150° C. for 20 hours. After the reaction mixture was cooled to room temperature, water was added, pH of the reaction mixture was adjusted at 5 by concentrated hydrochloric acid and was subjected to extraction with chloroform. The organic layer was washed with sodium chloride solution and dried, concentrated to give residue which was purified by silica gel column chromatography (eluent: chloroform/methanol=50/1). The more polar product obtained was recrystallized from ethanol/ether to give 2.67 g (yield: 49%) of Compound 47 as white crystals.

$^1$H-NMR (CDCl$_3$) δ: 8.02 (d, 1H, J=2.0 Hz), 7.49 (dd, 1H, J=8.9, 2.0 Hz), 7.09 (d, 1H, J=8.9 Hz), 7.07(s, 2H), 5.29–5.20(m, 1H), 4.23–4.13(m, 4H), 3.84–3.79(m, 8H), 3.58 (s, 3H), 3.14–2.96 (m, 4H), 2.42 (s, 3H), 1.81–1.78 (br.-d, 2H), 1.50 (t, 3H, J=7.0 Hz).

IR (KBr tab.)(cm$^{-1}$): 1709, 1657, 1513, 1440, 1242.

Melting Point (ethanol-ether): 202–203° C.

EXAMPLE 48

3-[1-(6-Ethoxy-7-methoxy-2-morpholino-4-quinazolinyl)-4-piperidinyl]-1,2,3,4-tetrahydro-1,6-dimethyl-2,4-dioxoquinazoline (Compound 48)

In 2.2 ml of DMF was dissolved 335 mg (0.61 mmol) of Compound 47 obtained in Example 47, 25 mg (0.61 mmol) of 60% sodium hydride was added at ice-cooling, and stirred at ice-cooling for 20 minutes. 0.042 ml (0.67 mmol) of methyl iodide was added to the above reaction mixture and stirred at room temparature for 2 hours. Saturated ammonium chloride solution was added and resulting precipitate was collected by filtration, washed with water, dried at heating, purified by silica gel column chromatography (eluent: chloroform/methanol=100/1) and recrystallized from ethanol/ether to give 168 mg (yield: 49%) of Compound 48 as white crystals.

$^1$H-NMR (CDCl$_3$) δ: 8.02 (d, 1H, J=1.5 Hz), 7.49 (dd, 1H, J=8.5, 1.5 Hz), 7.09 (d, 1H, J=8.5 Hz), 7.09 (s, 1H), 6.95 (s, 1H), 5.26–5.18 (m, 1H), 4.27–4.24 (br.-d, 2H), 4.13 (q, 2H, J=7.0 Hz), 3.97 (s, 3H), 3.89–3.82 (m, 8H), 3.58 (s, 3H), 3.15–2.96 (m, 4H), 2.42 (s, 3H), 1.81–1.78 (br.-d, 2H), 1.51 (t, 3H, J=7.0 Hz).

IR (KBr tab.)(cm$^{-1}$): 1701, 1655, 1564, 1485, 1439, 1238.

Melting Point (ethanol-ether): 226–227° C.

EXAMPLE 49

3-[1-(6-Ethoxy-2-morpholino-7-propoxy-4-quinazolinyl)-4-piperidinyl]-1,2,3,4-tetrahydro-1,6-dimethyl-2,4-dioxoquinazoline (Compound 49)

The same procedure as in Example 48 was repeated, using 335 mg (0.61 mmol) of Compound 47 obtained in Example 47, except that propyl iodide was used in place of methyl iodide, to give 164 mg (yield: 46%) of Compound 49 as white crystals.

$^1$H-NMR (CDCl$_3$) δ: 8.02 (d, 1H, J=2.0 Hz), 7.49 (dd, 1H, J=8.6, 2.0 Hz), 7.11 (s, 1H), 7.09(d, 1H, J=8.6 Hz), 6.92 (s, 1H), 5.26–5.19 (m, 1H), 4.28–4.25 (br.-d, 2H), 4.15–4.05(m, 4H), 3.83–3.81 (m, 8H), 3.58 (s, 3H), 3.14–2.95 (m, 4H), 2.42 (s, 3H), 1.96–1.85 (m, 2H), 1.82–1.78 (br.-d, 2H), 1.48 (t, 3H, J=7.0 Hz), 1.06(t, 3H, J=7.0 Hz).

IR (KBr tab.)(cm$^{-1}$): 1701, 1657, 1560, 1437, 1238.

Melting Point (ethanol-ether): 210–211° C.

EXAMPLE 50

3-[1-(6-Ethoxy-7-isopropoxy-2-morpholino-4-quinazolinyl)-4-piperidinyl]-1,2,3,4-tetrahydro-1,6-dimethyl-2,4-dioxoquinazoline (Compound 50)

The same procedure as in Example 48 was repeated, using 335 mg (0.61 mmol) of Compound 47 obtained in Example 47, except that isopropyl iodide was used in place of methyl iodide, to give 112 mg (yield: 31%) of Compound 50 as white crystals.

$^1$H-NMR (CDCl$_3$) δ: 8.02 (d, 1H, J=1.7 Hz), 7.49 (dd, 1H, J=8.6, 1.7 Hz), 7.12 (s, 1H), 7.09 (d, 1H, J=8.6 Hz), 6.92 (s, 1H), 5.26–5.19 (m, 1H), 4.74–4.68 (m, 1H), 4.27–4.24(br.-d, 2H), 4.10 (q, 2H, J=7.0 Hz), 3.83–3.81 (m, 8H), 3.58 (s, 3H), 3.09–2.99 (m, 4H), 2.42 (s, 3H), 1.81–1.77 (br.-d, 2H), 1.46(t, 3H, J=7.0 Hz), 1.44 (d, 6H, J=6.0 Hz).

IR (KBr tab.)(cm$^{-1}$): 1701, 1659, 1556, 1481, 1441, 1236.

Melting Point (ethanol-ether): 194–195° C.

EXAMPLE 51

3-[1-(7-Butoxy-6-ethoxy-2-morpholino-4-quinazolinyl)-4-piperidinyl]-1,2,3,4-tetrahydro-1,6-dimethyl-2,4-dioxoquinazoline (Compound 51)

The same procedure as in Example 48 was repeated, using 335 mg (0.61 mmol) of Compound 47 obtained in Example 47, except that butyl iodide was used in place of methyl iodide, to give 144 mg (yield: 39%) of Compound 51 as white crystals.

$^1$H-NMR (CDCl$_3$) δ: 8.02 (d, 1H, J=2.0 Hz), 7.49 (dd, 1H, J=8.6, 2.0 Hz), 7.11 (s, 1H), 7.09 (d, 1H, J=8.6 Hz), 6.92 (s, 1H), 5.26–5.19 (m, 1H), 4.27–4.25 (br.-d, 2H), 4.23–4.07(m, 4H), 3.83–3.81 (m, 8H), 3.58 (s, 3H), 3.14–2.99 (m, 4H), 2.42 (s, 3H), 1.93–1.81 (m, 2H), 1.81–1.78(br.-d, 2H), 1.56–1.51(m, 2H), 1.47(t, 3H, J=7.0 Hz), 0.99 (t, 3H, J=7.0 Hz).

IR (KBr tab.)(cm$^{-1}$): 1701, 1659, 1558, 1485, 1441, 1238.

Melting Point (ethanol-ether): 195–196° C.

EXAMPLE 52

3-[1-(7-Acetoxy-6-ethoxy-2-morpholino-4-quinazolinyl)-4-piperidinyl]-1,2,3,4-tetrahydro-1,6-dimethyl-2,4-dioxoquinazoline (Compound 52)

In 3 ml of pyridine was dissolved 360 mg (0.66 mmol) of Compound 47 obtained in Example 47, 0.12 ml (1.32 mmol) of acetic anhydride was added, and the mixture was stirred at room temperature for 4 hours. The solvent was removed at reduced pressure and water was added to the residue, the resulting precipitate was collected by filtration, washed with water, dried at heating and recrystallized from ethanol to give 205 mg (yield: 53%) of Compound 52 as white crystals.

$^1$H-NMR (CDCl$_3$) δ: 8.01 (d, 1H, J=2.0 Hz), 7.49 (dd, 1H, J=8.6, 2.0 Hz), 7.22 (s, 1H), 7.17(s, 1H), 7.09 (d, 1H, J=8.6 Hz), 5.29–5.21 (m, 1H), 4.30–4.26 (br.-d, 2H), 4.08 (q, 2H, J=7.0 Hz), 3.83–3.79 (m, 8H), 3.58 (s, 3H), 3.16–2.99 (m, 4H), 2.42 (s, 3H), 2.34(s, 3H), 1.82–1.78 (br.-d, 2H), 1.42 (t, 3H, J=7.0 Hz).

IR (KBr tab.)(cm$^{-1}$): 1767, 1699, 1657, 1558, 1483, 1434, 1236.

Melting Point (ethanol): 226–227° C.

EXAMPLE 53

3-{1-[7-(2-Dimethylaminoethyl)oxy-6-ethoxy-2-morpholino-4-quinazolinyl]-4-piperidinyl}-1,2,3,4-tetrahydro-1,6-dimethyl-2,4-dioxoquinazoline (Compound 53)

The same procedure as in Example 48 was repeated, using 360 mg (0.66 mmol) of Compound 47 obtained in Example 47 and 2 equivalents of sodium hydride (60% in oil), except that 2-dimethylaminoethyl chloride hydrochloride was used in place of methyl iodide and reaction temperature was 60° C. in place of room temperature, to give 127 mg (yield: 31%) of Compound 53 as white crystals.

$^1$H-NMR (CDCl$_3$) δ: 8.02 (d, 1H, J=2.0 Hz), 7.49 (dd, 1H, J=8.6, 2.0 Hz), 7.09 (d, 1H, J=8.6 Hz), 7.09(s, 1H), 6.97 (s, 1H), 5.28–5.21 (m, 1H), 4.28–4.21 (m, 4H), 4.10 (q, 2H, J=7.0 Hz), 3.85–3.80 (m, 8H), 3.58 (s, 3H), 3.15–2.99 (m, 4H), 2.91–2.87 (m, 2H), 2.42 (s, 3H), 2.40(s, 6H), 1.82–1.78 (br.-d, 2H), 1.48(t, 3H, J=7.0 Hz).

IR (KBr tab.)(cm$^{-1}$): 1699, 1657, 1562, 1483, 1439, 1238.

Melting Point (ethanol-ether): 197–199° C.

EXAMPLE 54

3-[1-(6-Ethoxy-7-ethoxycarbonylmethoxy-2-morpholino-4-quinazolinyl)-4-piperidinyl]-1,2,3,4-tetrahydro-1,6-dimethyl-2,4-dioxoquinazoline (Compound 54)

The same procedure as in Example 48 was repeated, using 3.90 g (7.13 mmol) of Compound 47 obtained in Example 47, except that ethyl bromoacetate was used in place of methyl iodide, to give 2.81 g (yield: 62%) of Compound 54 as white crystals.

$^1$H-NMR (CDCl$_3$) δ: 8.02 (d, 1H, J=2.0 Hz), 7.49 (dd, 1H, J=8.6, 2.0 Hz), 7.13 (s, 1H), 7.09 (d, 1H, J=8.6 Hz), 6.81 (s, 1H), 5.27–5.18 (m, 1H), 4.78(s, 2H), 4.33–4.24 (m, 4H), 4.15 (q, 2H, J=7.0 Hz), 3.83–3.80 (m, 8H), 3.58 (s, 3H), 3.14–2.96 (m, 4H), 2.42 (s, 3H), 1.81–1.77 (br.-d, 2H), 1.50 (t, 3H, J=7.0 Hz), 1.31 (t, 3H, J=7.0 Hz).

IR (KBr tab.)(cm$^{-1}$): 1762, 1699, 1654, 1560, 1439, 1240.

Melting Point (ethanol-ether): 179–180° C.

EXAMPLE 55

3-{1-[6-Ethoxy-7-(2-hydroxyethyl)oxy-2-morpholino-4-quinazolinyl]-4-piperidinyl}-1,2,3,4-tetrahydro-1,6-dimethyl-2,4-dioxoquinazoline (Compound 55)

In 20 ml of ethanol was dissolved 2.10 g (3.32 mmol) of Compound 54 obtained in Example 54, excess sodium borohydride was added, and the mixture was stirred under heating at reflux for 1 hour. After cooling, the solvent was removed, water was added and the mixture was subjected to extraction with ethyl acetate. The organic layer was washed with sodium chloride solution, dried and concentrated to give residue. The residue was purified by silica gel column chromatography(eluent: chloroform/methanol=100/1) and recrystallized from ethanol to give 1.29 g (yield: 66%) of Compound 55 as white crystals.

$^1$H-NMR (CDCl$_3$) δ: 8.01 (d, 1H, J=2.0 Hz), 7.49 (dd, 1H, J=8.3, 2.0 Hz), 7.11 (s, 1H), 7.09 (d, 1H, J=8.3 Hz), 6.96 (s, 1H), 5.28–5.21 (m, 1H), 4.27–4.20 (m, 4H), 4.12 (q, 2H, J=7.0 Hz), 4.05–4.02 (m, 2H), 3.84–3.79 (m, 8H), 3.58 (s, 3H), 3.15–2.96 (m, 4H), 2.42 (s, 3H), 1.82–1.78 (br.-d, 2H), 1.49 (t, 3H, J=7.0 Hz).

IR (KBr tab.)(cm$^{-1}$): 1701, 1655, 1560, 1483, 1439, 1238.

Melting Point (ethanol): 236–237° C.

EXAMPLE 56

3-[1-(7-Carboxymethyloxy-6-ethoxy-2-morpholino-4-quinazolinyl)-4-piperidinyl]-1,2,3,4-tetrahydro-1,6-dimethyl-2,4-dioxoquinazoline (Compound 56)

In 30 ml of methanol was dissolved 900 mg (1.42 mmol) of Compound 54 obtained in Example 54, 15 ml of 2N-sodium hydroxide was added, and the mixture was stirred under heating at reflux for 4 hour. After cooling, 4N-hydrochloric acid was added to the reaction mixture and the mixtute was neutralized and subjected to extraction with chloroform. The organic layer was washed, dried and concentrated to give the residue. Ether was added to the above residue to give the precipitate which was collected by filtration and dried to give 870 mg (yield: 100%) of Compound 56 as white crystals.

$^1$H-NMR (CDCl$_3$) δ: 8.10 (s, 1H), 7.99(d, 1H, J=1.7 Hz), 7.51 (dd, 1H, J=8.6, 1.7 Hz), 7.11 (d, 1H, J=8.6 Hz), 7.11(s, 1H), 5.42–5.34 (m, 1H), 4.91(s, 2H), 4.68–4.63(br.-d, 2H), 4.16–4.06 (m, 6H), 3.85–3.82 (m, 4H), 3.58 (s, 3H), 3.44–3.35 (br.-t, 3H), 2.99–2.87(m, 2H), 2.42 (s, 3H), 1.93–1.90 (br.-d, 2H), 1.48 (t, 3H, J=7.0 Hz).

IR (KBr tab.)(cm$^{-1}$): 3600(br), 1699, 1653, 1593, 1458, 1270.

Melting Point (ether): 218–220° C.

EXAMPLE 57

3-{1-[6-Ethoxy-7-(N-isopropylcarbamoyl)methoxy-2-morpholino-4-quinazolinyl]-4-piperidinyl}-1,2,3,4-tetrahydro-1,6-dimethyl-2,4-dioxoquinazoline (Compound 57)

In 2.2 ml of methylene chloride was dissolved 300 mg (0.50 mmol) of Compound 56 obtained in Example 56, and 0.11 ml (1.51 mmol) of thionyl chloride was dropwised at ice-cooling. The mixture was stirred at 40° C. for 1 hour, and the solvent was removed at reduced pressure to give the corresponding acid chloride derivatives. In 3 ml of methylene chloride were dissolved 0.05 ml (0.60 mmol) of isopropylamine and 0.35 ml (2.51 mmol) of tirethylamine, and the above acid chloride derivatives in 3 ml of methylene chloride was dropwised at ice-cooling. The reaction mixture was stirred at room temperature for 2 hours, and poured into ice-cooling water and the mixture was subjected to extraction with methylene chloride. The organic layer was washed with sodium chloride solution, dried, and concentrated to give residue. The residue was purified by silica gel column chromatography(eluent: chloroform/methanol=50/1) and recrystallized from ethanol/ether to give 57 mg (yield: 18%) of Compound 57 as white crystals.

$^1$H-NMR (CDCl$_3$) δ: 8.02 (d, 1H, J=2.0 Hz), 7.49 (dd, 1H, J=8.6, 2.0 Hz), 7.12(s, 1H), 7.09 (d, 1H, J=8.6 Hz), 6.92 (s, 1H), 5.29–5.21 (m, 1H), 4.56(s, 2H), 4.26–4.22(br.-d, 2H), 4.19–4.03 (m, 3H), 3.83–3.78 (m, 8H), 3.59 (s, 3H), 3.21–3.00 (m, 4H), 2.43 (s, 3H), 1.83–1.79 (br.-d, 2H), 1.52 (t, 3H, J=7.0 Hz), 1.22(d, 6H, J=6.0 Hz).

IR (KBr tab.)(cm$^{-1}$): 1701, 1655, 1560, 1483, 1439, 1236.

Melting Point (ethanol-ether): 160–163° C.

EXAMPLE 58

3-[1-(6-Ethoxy-2-morpholino-7-pyrrolidinylcarbonylmethoxy-4-quinazolinyl)-4-piperidinyl]-1,2,3,4-tetrahydro-1,6-dimethyl-2,4-dioxoquinazoline (Compound 58)

The same procedure as in Example 57 was repeated, using 300 mg (0.50 mmol) of Compound 56 obtained in Example 56, except that pyrrolidine was used in place of isopropylamine, to give 48 mg (yield: 15%) of Compound 58 as white crystals.

$^1$H-NMR (CDCl$_3$) δ: 8.02 (d, 1H, J=2.0 Hz), 7.49 (dd, 1H, J=8.6, 2.0 Hz), 7.12 (s, 1H), 7.09(d, 1H, J=8.6 Hz), 6.91 (s, 1H), 5.28–5.20 (m, 1H), 4.77(s, 2H), 4.28–4.24(br.-d, 2H), 4.13 (q, 2H, J=7.0 Hz), 3.83–3.80 (m, 10H), 3.60–3.53(m, 2H), 3.58 (s, 3H), 3.10–2.99 (m, 4H), 2.42 (s, 3H), 2.02–1.85 (m, 4H), 1.82–1.78 (br.-d, 2H), 1.48(t, 3H, J=7.0 Hz).

IR (KBr tab.)(cm$^{-1}$): 1703, 1659, 1556, 1479, 1441, 1236.

Melting Point (ethanol-ether): 145–147° C.

EXAMPLE 59

3-[1-(7-Ethoxy-6-hydroxy-2-morpholino-4-quinazolinyl)-4-piperidinyl]-1,2,3,4-tetrahydro-1,6-dimethyl-2,4-dioxoquinazoline (Compound 59)

Less polar product eluted from silica gel column chromatography(eluent: chloroform/methanol=50/1) in Example 47 was recrystallized from ethanol/ether to give 380 mg (yield: 7%) of Compound 59 as white crystals.

$^1$H-NMR (CDCl$_3$) δ: 8.02 (d, 1H, J=2.0 Hz), 7.49 (dd, 1H, J=8.6, 2.0 Hz), 7.23 (s, 1H), 7.09(d, 1H, J=8.6 Hz), 6.95 (s, 1H), 5.28–5.21(m, 1H), 4.32–4.19(m, 4H), 3.83–3.81 (m, 8H), 3.58 (s, 3H), 3.14–3.00 (m, 4H), 2.42 (s, 3H), 1.80–1.77 (br.-d, 2H), 1.50 (t, 3H, J=7.0 Hz).

IR (KBr tab.)(cm$^{-1}$): 1701, 1655, 1514, 1475, 1441, 1238.

Melting Point (ethanol-ether): 198–200° C.

EXAMPLE 60

3-[1-(7-Ethoxy-6-ethoxycarbonylmethoxy-2-morpholino-4-quinazolinyl)-4-piperidinyl]-1,2,3,4-tetrahydro-1,6-dimethyl-2,4-dioxoquinazoline (Compound 60)

The same procedure as in Example 48 was repeated, except that 290 mg (0.53 mmol) of Compound 59 obtained in Example 59 was used in place of Compound 47 obtained in Example 47, and ethyl bromoacetate was used in place of methyl iodide, to give 216 mg (yield: 64%) of Compound 60 as white crystals.

$^1$H-NMR (CDCl$_3$) δ: 8.01 (d, 1H, J=2.0 Hz), 7.49 (dd, 1H, J=8.6, 2.0 Hz), 7.16 (s, 1H), 7.09 (d, 1H, J=8.6 Hz), 6.93 (s, 1H), 5.28–5.22 (m, 1H), 4.70(s, 2H), 4.31–4.16 (m, 6H), 3.84–3.79 (m, 8H), 3.57 (s, 3H), 3.14–2.97 (m, 4H), 2.42 (s, 3H), 1.79–1.75 (br.-d, 2H), 1.51 (t, 3H, J=7.0 Hz), 1.29 (t, 3H, J=7.0 Hz).

IR (KBr tab.)(cm$^{-1}$): 1757, 1701, 1657, 1556, 1473, 1444, 1236.

Melting Point (ethanol-ether): 134–136° C.

EXAMPLE 61

3-{1-[7-Ethoxy-6-(2-hydorxyethyl)oxy-2-morpholino-4-quinazolinyl]-4-piperidinyl}-1,2,3,4-tetrahydro-1,6-dimethyl-2,4-dioxoquinazoline (Compound 61)

The same procedure as in Example 55 was repeated, except that 175 mg (0.28 mmol) of Compound 60 obtained in Example 60 was used in place of Compound 54 obtained in Example 54, to give 101 mg (yield: 62%) of Compound 61 as white crystals.

$^1$H-NMR (CDCl$_3$) δ: 8.01 (d, 1H, J=2.0 Hz), 7.49 (dd, 1H, J=8.6, 2.0 Hz), 7.22 (s, 1H), 7.09 (d, 1H, J=8.6 Hz), 6.94 (s, 1H), 5.28–5.21 (m, 1H), 4.27–4.15 (m, 6H), 3.96–3.93 (m, 2H), 3.84–3.80 (m, 8H), 3.58 (s, 3H), 3.15–2.99 (m, 4H), 2.42 (s, 3H), 1.82–1.78 (br.-d, 2H), 1.51 (t, 3H, J=7.0 Hz).

IR (KBr tab.)(cm$^{-1}$): 1699, 1655, 1560, 1473, 1437, 1238.

Melting Point (ethanol): 210–211° C.

EXAMPLE 62

Tablets

Tablets having the following composition were prepared in a conventional manner.

Compound 10 (40 g) was mixed with 286.8 g of lactose and 60 g of potato starch, followed by addition of 120 g of a 10% aqueous solution of hydroxypropyl cellulose. The resulting mixture was kneaded, granulated, and then dried by a conventional method. The granules were refined to give granules to be tabletted. After mixing the granules with 1.2 g of magnesium stearate, the mixture was formed into tablets each containing 20 mg of the active ingredient by using a tablet maker (Model RT-15, Kikusui) having pestles of 8 mm diameter.

| Composition of One Tablet | |
|---|---|
| Compound 10 | 20 mg |
| Lactose | 143.4 mg |
| Potato Starch | 30 mg |
| Hydroxypropyl Cellulose | 6 mg |
| Magnesium Stearate | 0.6 mg |
| | 200 mg |

EXAMPLE 63

Capsules

Capsules having the following composition were prepared in a conventional manner.

Compound 10 (200 g) was mixed with 995 g of Avicel and 5 g of magnesium stearate. The mixture was put in hard capsules No. 4 each having a capacity of 120 mg by using a capsule filler (Model LZ-64, Zanasi) to give capsules each containing 20 mg of the active ingredient.

| Composition of One Capsule | |
|---|---|
| Compound 10 | 20 mg |
| Avicel | 99.5 mg |
| Magnesium Stearate | 0.5 mg |
| | 120 mg |

EXAMPLE 64

Injections

Injections having the following composition were prepared in a conventional manner.

Compound 10 (1 g) was dissolved in 100 g of purified soybean oil, followed by addition of 12 g of purified egg yolk lecithin and 25 g of glycerine for injection. The resulting mixture was made up to 1,000 ml with distilled water for injection, thoroughly mixed, and emulsified by a conventional method. The resulting dispersion was subjected to aseptic filtration by using 0.2 μm disposable membrane filters, and then aseptically put into glass vials in 2 ml portions to give injections containing 2 mg of the active ingredient per vial.

| Composition of One Injectin Vial | |
|---|---|
| Compound 10 | 2 mg |
| Purified Soybean Oil | 200 mg |
| Purified Egg Yolk Lecithin | 24 mg |
| Glycerine for Injection | 50 mg |
| Distilled Water for Injection | 1.72 ml |
| | 2.00 ml |

EXAMPLE 65

Rectal Suppositories

Preparations for rectal administration having the following composition were prepared in a conventional manner.

Witepsol™H15 (678.8 g, Dynamit Nobel) and Witepsol™E75 (290.9 g, Dynamit Nobel) were melted at 40–50° C. In the melt were uniformly dispersed 2.5 g of Compound 10, 13.6 g of potassium primary phosphate and 14.2 g of sodium secondary phosphate. The resulting dispersion was put into plastic molds and gradually cooled to give suppositories for rectal administration each containing 2.5 mg of the active ingredient.

| Composition of One Suppository Preparation | |
|---|---|
| Compound 10 | 2.5 mg |
| Witepsol ™ H15 | 678.8 mg |
| Witepsol ™ E75 | 290.9 mg |
| Potassium Primary Phosphate | 13.6 mg |
| Sodium Secondary Phosphate | 14.2 mg |
| | 1,000 mg |

REFERENCE EXAMPLE 1

3-[1-(2-Chloro-6,7-dimethoxy-4-quinazolinyl)-4-piperidinyl]-1,2,3,4-tetrahydro-1,6-dimethyl-2,4-dioxoquinazoline (Compound a)

Step 1:

In 50 ml of 48% hydrobromic acid was dissolved 5.0 g (14.5 mmol) of 3-(1-ethoxycarbonyl-4-piperidinyl)-1,2,3,4-tetrahydro-1,6-dimethyl-2,4-dioxoquinazoline (Compound g) obtained in Reference Example 7, and the solution was heated under reflux for 1.5 hours. After evaporation of the solvent, ethanol was added to the residue. The precipitated crystals were collected by filtration to give 5.04 g (yield: 99%) of 1,2,3,4-tetrahydro-1,6-dimethyl-2,4-dioxo-3-(4-piperidinyl)quinazoline hydrobromide as white crystals.

$^1$H-NMR (DMSO-d$_6$) δ: 7.85 (d, 1H, J=2.0 Hz), 7.60 (dd, 1H, J=8.6, 2.0 Hz), 7.35 (d, 1H, J=8.6 Hz), 5.16–5.07 (m, 1H), 3.49 (s, 3H), 3.41–3.36 (br.-d, 2H), 3.13–3.05 (m, 2H), 2.86–2.73 (m, 2H), 2.38 (s, 3H), 1.81–1.77(br.-d, 2H).

IR (KBr tab.)(cm$^{-1}$): 1696, 1627, 1512.

Melting Point (ethanol): >300° C.

Step 2:

In 40 ml of methanol were suspended 2.0 g (5.65 mmol) of the hydrobromide obtained in Step 1 and 1.47 g (5.65 mmol) of 2,4-dichloro-6,7-dimethoxyquinazoline, and 2.0 ml (14.1 mmol) of triethylamine was added to the suspension, followed by heating under reflux for 2 hours. After cooling, the solvent was evaporated and water was added to the residue. The precipitated crystals were collected by filtration and washed with water and methanol to give 2.27 g (yield: 81%) of Compound a as white crystals.

$^1$H-NMR (CDCl$_3$) δ: 8.01 (d, 1H, J=1.0 Hz), 7.49 (dd, 1H, J=8.5, 1.0 Hz), 7.26 (s, 1H), 7.14 (s, 1H), 7.10 (d, 1H, J=8.5 Hz), 5.38–5.26 (m, 1H), 4.50–4.45 (br.-d, 2H), 4.01 (s, 3H), 3.99 (s, 3H), 3.58 (s, 3H), 3.29–3.20 (br.-t, 2H), 3.11–2.96 (m, 2H), 2.42 (s, 3H), 1.90–1.85 (br.-d, 2H).

IR (KBr tab.)(cm$^{-1}$): 1706, 1655, 1512, 1480, 1218.

Melting Point (ether): 234–236° C.

REFERENCE EXAMPLE 2

3-[1-(2-Chloro-6,7-diethoxy-4-quinazolinyl)-4-piperidinyl]-1,2,3,4-tetrahydro-1,6-dimethyl-2,4-dioxoquinazoline (Compound b)

The same procedure as in Reference Example 1 was repeated, except that 2,4-dichloro-6,7-diethoxyquinazoline was used in place of 2,4-dichloro-6,7-dimethoxyquinazoline, to give Compound b as pale yellow crystals.

$^1$H-NMR (CDCl$_3$) δ: 8.01 (d, 1H, J=1.3 Hz), 7.49 (dd, 1H, J=8.6, 1.3 Hz), 7.16 (s, 1H), 7.15 (s, 1H), 7.09 (d, 1H, J=8.6 Hz), 5.31–5.25 (m, 1H), 4.46–4.39 (br.-d, 2H), 4.22 (q, 2H, J=7.0 Hz), 4.17 (q, 2H, J=7.0 Hz), 3.58 (s, 3H), 3.25–3.16 (br.-t, 2H), 3.10–2.99 (m, 2H), 2.42 (s, 3H), 1.88–1.83 (br.-d, 2H), 1.53 (t, 3H, J=7.0 Hz), 1.52 (t, 3H, J=7.0 Hz).

IR (KBr tab.)(cm$^{-1}$): 1694, 1657, 1511, 1336, 1033.

Melting Point (methanol-water): 209–210° C.

REFERENCE EXAMPLE 3

3-[1-(2-Chloro-6,7-methylenedioxy-4-quinazolinyl)-4-piperidinyl]-1,2,3,4-tetrahydro-1,6-dimethyl-2,4-dioxoquinazoline (Compound c)

The same procedure as in Reference Example 1 was repeated, except that 2,4-dichloro-6,7-methylenedioxyquinazoline was used in place of 2,4-dichloro-6,7-dimethoxyquinazoline, to give Compound c as white crystals.

$^1$H-NMR (CDCl$_3$) δ: 8.01 (d, 1H, J=1.5 Hz), 7.49 (dd, 1H, J=8.6, 1.5 Hz), 7.18 (s, 1H), 7.15 (s, 1H), 7.09 (d, 1H, J=8.6 Hz), 6.12 (s, 2H), 5.34–5.24 (m, 1H), 4.37–4.32 (br.-d, 2H), 3.58 (s, 3H), 3.22–2.96 (m, 4H), 2.42 (s, 3H), 1.86–1.82 (br.-d, 2H).

IR (KBr tab.)(cm$^{-1}$): 1703, 1649, 1620, 1509, 1464.

Melting Point (ethyl acetate-ether): 278–280° C.

REFERENCE EXAMPLE 4

3-[1-(2-Chloro-6,7-dipropoxy-4-quinazolinyl)-4-piperidinyl]-1,2,3,4-tetrahydro-1,6-dimethyl-2,4-dioxoquinazoline (Compound d)

The same procedure as in Reference Example 1 was repeated, except that 2,4-dichloro-6,7-dipropoxyquinazoline was used in place of 2,4-dichloro-6,7-dimethoxyquinazoline, to give Compound d as white crystals.

$^1$H-NMR (CDCl$_3$) δ: 8.02 (d, 1H, J=2.0 Hz), 7.49 (dd, 1H, J=8.6, 2.0 Hz), 7.16 (s, 1H), 7.14 (s, 1H), 7.09 (d, 1H, J=8.6 Hz), 5.35–5.10 (m, 1H), 4.46–4.40 (br.-d, 2H), 4.09 (t, 2H, J=6.5 Hz), 4.05 (t, 2H, J=6.5 Hz), 3.58 (s, 3H), 3.25–3.16 (br.-t, 2H), 3.08–2.99 (m, 2H), 2.42 (s, 3H), 1.95–1.84 (m, 6H), 1.09 (t, 3H, J=6.5 Hz), 1.08 (t, 3H, J=6.5 Hz).

IR (KBr tab.)(cm$^{-1}$): 1700, 1665, 1655, 1510.

Melting Point (ether): 171–173° C.

REFERENCE EXAMPLE 5

3-[1-(2-Chloro-6,7-diisopropoxy-4-quinazolinyl)-4-piperidinyl]-1,2,3,4-tetrahydro-1,6-dimethyl-2,4-dioxoquinazoline (Compound e)

The same procedure as in Reference Example 1 was repeated, except that 2,4-dichloro-6,7-diisopropoxyquinazoline was used in place of 2,4-dichloro-6,7-dimethoxyquinazoline, to give Compound e as white crystals.

$^1$H-NMR (CDCl$_3$) δ: 8.01 (d, 1H, J=1.5 Hz), 7.49 (dd, 1H, J=8.5, 1.5 Hz), 7.26 (s, 1H), 7.18 (s, 1H), 7.09 (d, 1H, J=8.5 Hz), 5.32–5.24 (m, 1H), 4.69 (sept, 1H, J=6.0 Hz), 4.55 (sept, 1H, J=6.0 Hz), 4.52–4.50 (br.-d, 2H), 3.58 (s, 3H), 3.26–3.18 (br.-t, 2H), 3.09–2.94 (m, 2H), 2.42 (s, 3H), 1.87–1.83 (br.-d, 2H), 1.44 (d, 3H, J=6.0 Hz), 1.38 (d, 3H, J=6.0 Hz).

IR (KBr tab.)(cm$^{-1}$): 1699, 1657, 1479, 1460, 1246.

Melting Point (ether): 130–132° C.

REFERENCE EXAMPLE 6

3-[1-(7-Benzyloxy-2-chloro-6-methoxy-4-quinazolinyl)-4-piperidinyl]-1,2,3,4-tetrahydro-1,6-dimethyl-2,4-dioxoquinazoline (Compound f)

The same procedure as in Reference Example 1 was repeated, except that 7-benzyloxy-2,4-dichloro-6-methoxyquinazoline was used in place of 2,4-dichloro-6,7-dimethoxyquinazoline, to give Compound f as white crystals.

$^1$H-NMR (CDCl$_3$) δ: 8.01 (d, 1H, J=1.5 Hz), 7.51–7.32 (m, 6H), 7.21 (s, 1H), 7.16 (s, 1H), 7.09 (d, 1H, J=8.3 Hz), 5.40–5.20 (m, 1H), 5.27 (s, 2H), 4.45–4.41 (br.-d, 2H), 3.98 (s, 3H), 3.58 (s, 3H), 3.26–3.17 (br.-t, 2H), 3.10–3.00 (m, 2H), 2.42 (s, 3H), 1.88–1.85 (br.-d, 2H).

IR (KBr tab.)(cm$^{-1}$): 1701, 1645, 1503, 1429.

Melting Point (ethyl acetate-ether): 146–150° C.

REFERENCE EXAMPLE 7

3-(1-Ethoxycarbonyl-4-piperidinyl)-1,2,3,4-tetrahydro-1,6-dimethyl-2,4-dioxoquinazoline (Compound g)

The same procedure as in Example 30 was repeated using 1.0 g (3.02 mmol) of 3-(1-ethoxycarbonyl-4-piperidinyl)-1,2,3,4-tetrahydro-6-methyl-2,4-dioxoquinazoline obtained by the method described in Chem. Pharm. Bull. 34, 1907–1916 (1986) to give 745.6 mg (yield: 72%) of Compound g as white crystals.

$^1$H-NMR (CDCl$_3$) δ: 7.99 (d, 1H, J=2.0 Hz), 7.45 (dd, 1H, J=8.6, 2.0 Hz), 7.07 (d, 1H, J=8.6 Hz), 5.17–5.06 (m, 1H), 4.40–4.20 (m, 2H), 4.14 (q, 2H, J=7.3 Hz), 3.55 (s, 3H), 2.96–2.82 (br.-t, 2H), 2.77–2.64 (m, 2H), 2.41 (s, 3H), 1.66–1.61 (br.-d, 2H), 1.27 (t, 3H, J=7.3 Hz).

IR (KBr tab.)(cm$^{-1}$): 1702, 1680, 1658, 1240.

Melting Point (ether): 156–157° C.

REFERENCE EXAMPLE 8

3-(1-Ethoxycarbonyl-4-piperidinyl)methyl-1,2,3,4-tetrahydro-1,6-dimethyl-2,4-dioxoquinazoline (Compound k)

The same procedure as in Reference Example 7 was repeated, except that 2.74 g (7.94 mmol) of 3-(1-ethoxycarbonyl-4-piperidinyl)methyl-1,2,3,4-tetrahydro-6-methyl-2,4-dioxoquinazoline was used in place of 3-(1-ethoxycarbonyl-4-piperidinyl)-1,2,3,4-tetrahydro-6-methyl-2,4-dioxoquinazoline, to give 2.40 g (yield: 84%) of Compound k as white crystals.

$^1$H-NMR (CDCl$_3$) δ: 8.01 (s, 1H), 7.50 (d, 1H, J=8.6 Hz), 7.11 (d, 1H, J=8.6 Hz), 4.28–4.07 (m, 4H), 4.02 (d, 2H, J=7.3 Hz), 3.59 (s, 3H), 2.74–2.65 (br.-t, 2H), 2.42 (s, 3H), 2.10–1.96 (m, 1H), 1.66–1.62 (br.-d, 2H), 1.39–1.16 (m, 5H).

REFERENCE EXAMPLE 9

3-[1-(2-Chloro-6,7-dimethoxy-4-quinazolinyl)-4-piperidinyl]methyl-1,2,3,4-tetrahydro-1,6-dimethyl-2,4-dioxoquinazoline (Compound h)

The same procedure as in Reference Example 1 was repeated, except that Compound k obtained in Reference Example 8 was used in place of Compound g, to give Compound h as white crystals (overall yield: 64%).

$^1$H-NMR (CDCl$_3$) δ: 8.03 (s, 1H), 7.51 (d, 1H, J=8.6 Hz), 7.16 (s, 1H), 7.13 (d, 1H, J=8.6 Hz), 7.05 (s, 1H), 4.29–4.24 (br.-d, 2H), 4.12 (d, 2H, J=6.9 Hz), 3.99 (s, 3H), 3.97 (s, 3H), 3.61 (s, 3H), 3.12–3.04 (br.-t, 2H), 2.43 (s, 3H), 2.38–2.24 (m, 1H), 1.89–1.85 (br.-d, 2H), 1.71–1.64 (m, 2H).

Melting Point (methanol-water): 270–271° C.

REFERENCE EXAMPLE 10

1-(2-Chloro-6,7-dimethoxy-4-quinazolinyl)-4-[2-(5-methyl-2-nitrobenzoylamino)ethyl]piperidine (Compound m)

To 2.5 g (11.8 mmol) of 5-methyl-2-nitrobenzoic acid was added 10 ml of thionyl chloride, followed by heating at 100° C. for 1.5 hours. The solvent was evaporated under reduced pressure, and 50 ml of dichloromethane was added to the residue to prepare Solution A. In dichloroethane was dissolved 2.5 g of 4-(2-aminoethyl)-1-(2-chloro-6,7-dimethoxy-4-quinazolinyl)piperidine obtained by the method described in Chem. Pharm. Bull., 38, 3014–3019 (1990) and the literature cited therein. To this solution was added 9.7 ml of triethylamine, and after stirring at room temperature, Solution A was added dropwise to the mixture. The resulting mixture was subjected to reaction at room temperature for 30 minutes and then was added dropwise to water, followed by extraction with dichloromethane. The organic layer was washed and dried, and the solvent was evaporated under reduced pressure. The residue was washed with a solvent mixture of ethanol and ether to give 5.0 g (yield: 83%) of Compound m as white crystals.

¹H-NMR (CDCl₃) δ: 7.99 (d, 1H, J=8.2 Hz), 7.35 (d, 1H, J=8.2 Hz), 7.30 (s, 1H), 7.16 (s, 1H), 7.06 (s, 1H), 5.82 (br.-s, 1H, NH), 4.34–4.29 (br.-d, 2H), 3.99 (s, 3H), 3.98 (s, 3H), 3.61–3.54 (m, 2H), 3.20–3.10 (m, 2H), 2.46 (s, 3H), 1.99–1.94 (br.-d, 2H), 1.79–1.47 (m, 5H).

REFERENCE EXAMPLE 11

1-(6,7-Dimethoxy-2-morpholino-4-quinazolinyl)-4-[2-(5-methyl-2-nitrobenzoylamino)ethyl]piperidine (Compound n)

The same procedure as in Example 1 was repeated, except that 2.5 g (4.87 mmol) of Compound m obtained in Reference Example 10 was used, and N-methylpyrrolidinone was used as the solvent in place of dimethylformamide, to give 2.29 g (yield: 83%) of Compound n as white crystals.

¹H-NMR (CDCl₃) δ: 8.00 (d, 1H, J=8.2 Hz), 7.35 (d, 1H, J=8.2 Hz), 7.30 (s, 1H), 6.99 (s, 1H), 6.93 (br.-s, 1H), 5.74 (br.-s, 1H, NH), 4.17–4.12 (br.-d, 2H), 3.98 (s, 3H), 3.93 (s, 3H), 3.81 (br.-s, 8H), 3.61–3.48 (m, 2H), 3.07–2.99 (br.-t, 2H), 2.46 (s, 3H), 1.94–1.89 (br.-d, 2H), 1.70–1.32 (m, 5H).

REFERENCE EXAMPLE 12

1-[2-Bis(2-hydroxyethyl)amino-6,7-dimethoxy-4-quinazolinyl]-4-[2-(5-methyl-2-nitrobenzoylamino)ethyl]piperidine (Compound o)

The same procedure as in Reference Example 11 was repeated, except that 4.0 g (7.80 mmol) of Compound m was used, and diethanolamine was used in place of morpholine, to give 3.24 g (yield: 71%) of Compound o as white crystals.

¹H-NMR (CDCl₃) δ: 7.99 (d, 1H, J=8.6 Hz), 7.35 (d, 1H, J=8.6 Hz), 7.30 (s, 1H), 7.02 (br.-s, 1H), 6.95 (s, 1H), 5.86 (br.-s, 1H, NH), 4.21–4.16 (br.-d, 2H), 3.97 (s, 3H), 3.92 (s, 3H), 3.92–3.84 (m, 8H), 3.60–3.52 (m, 2H), 3.13–3.04 (br.-t, 2H), 2.47 (s, 3H), 1.98–1.93 (br.-d, 2H), 1.85–1.45 (m, 5H).

REFERENCE EXAMPLE 13

4-[2-(2-Amino-5-methylbenzoylamino)ethyl]-1-(6,7-dimethoxy-2-morpholino-4-quinazolinyl)piperidine (Compound i)

In 60 ml of ethanol was suspended 2.06 g (3.65 mmol) of Compound n obtained in Reference Example 11, and 500 mg of 10% palladium/carbon was added to the suspension, followed by stirring at room temperature for 20 hours in an atmosphere of hydrogen. The reaction mixture was filtered using a filter aid, and the filtrate was evaporated under reduced pressure to give 1.60 g (yield: 82%) of Compound i as white crystals.

¹H-NMR (CDCl₃) δ: 7.10 (s, 1H), 7.03 (d, 1H, J=8.2 Hz), 6.98 (s, 2H), 6.62 (d, 1H, J=8.2 Hz), 6.10 (br.-s, 1H), 4.18–4.14 (br.-d, 2H), 3.98 (s, 3H), 3.92 (s, 3H), 3.84–3.79 (m, 8H), 3.54–3.47 (m, 2H), 3.07–2.98 (br.-t, 2H), 2.24 (s, 3H), 1.93–1.89 (br.-d, 2H), 1.80–1.47 (m, 5H).

REFERENCE EXAMPLE 14

4-[2-(2-Amino-5-methylbenzoylamino)ethyl]-1-[2-bis(2-hydroxyethyl)amino-6,7-dimethoxy-4-quinazolinyl]piperidine (Compound j)

The same procedure as in Reference Example 13 was repeated, except that 2.87 g (4.93 mmol) of Compound o obtained in Reference Example 12 was used, to give 2.12 g (yield: 78%) of Compound j as white crystals.

¹H-NMR (CDCl₃) δ: 7.10 (s, 1H), 7.04 (d, 1H, J=8.2 Hz), 6.94 (s, 2H), 6.62 (d, 1H, J=8.2 Hz), 6.10 (br.-s, 1H), 4.15–4.10 (br.-d, 2H), 3.96 (s, 3H), 3.91 (s, 3H), 3.90–3.83 (m, 8H), 3.54–3.47 (m, 2H), 3.07–2.98 (br.-t, 2H), 2.24 (s, 3H), 1.96–1.91 (br.-d, 2H), 1.79–1.46 (m, 5H).

REFERENCE EXAMPLE 15

3-[1-(2-Chloro-6,7-diethoxy-4-quinazolinyl)-4-piperidinyl]-1,2,3,4-tetrahydro-2,4-dioxoquinazoline (Compound p)

The same procedure as in Reference Example 2 was repeated using 3-(1-ethoxycarbonyl-4-piperidinyl)-1,2,3,4-tetrahydro-2,4-dioxoquinazoline obtained by the method described in Chem. Pharm. Bull., 34, 1907–1916 (1986) to give Compound p as white crystals.

¹H-NMR (CDCl₃) δ: 9.78 (br.-s, 1H, NH), 8.12 (dd, 1H, J=6.9, 1.8 Hz), 7.63 (ddd, 1H, J=6.9, 6.9, 1.8 Hz), 7.24 (ddd, 1H, J=6.9, 6.9, 1.8 Hz), 7.19 (s, 1H), 7.15 (s, 1H), 7.03 (dd, 1H, J=6.9, 1.8 Hz), 5.33–5.24 (m, 1H), 4.49–4.44 (br.-d, 2H), 4.23 (q, 2H, J=7.0 Hz), 4.16 (q, 2H, J=7.0 Hz), 3.31–3.22 (br.-t, 2H), 3.09–2.97 (m, 2H), 1.89–1.86 (br.-d, 2H), 1.53 (t, 3H, J=7.0 Hz), 1.50 (t, 3H, J=7.0 Hz).

IR (KBr tab.)(cm⁻¹): 1708, 1659, 1560, 776.

Melting Point (ethyl acetate-ether): 248–250° C.

Compounds q-dd (Reference Examples 16–29) which are used in Examples 33–46 are obtained as white crystals according to the same procedure as in Reference Example 1, using the corresponding compounds obtained by the methods described in Chem. Pharm. Bull, 34, 1907–1916 (1986) and WO 94/19342 in place of 3-(1-ethoxycarbonyl-4-piperidinyl)-1,2,3,4-tetrahydro-1,6-dimethyl-2,4-dioxoquinazoline and using 2,4-dichloro-6,7-diethoxyquinazoline in place of 2,4-dichloro-6,7-dimethoxyquinazoline.

REFERENCE EXAMPLE 16

3-[1-(2-Chloro-6,7-diethoxy-4-quinazolinyl)-4-piperidinyl]-1,2,3,4-tetrahydro-1-methyl-2,4-dioxoquinazoline (Compound q)

¹H-NMR (CDCl₃) δ: 8.23 (dd, 1H, J=7.9, 1.3 Hz), 7.69 (ddd, 1H, J=7.9, 7.9, 1.3 Hz), 7.26 (ddd, 1H, J=7.9, 7.9, 1.3 Hz), 7.20 (dd, 1H, J=7.9, 1.3 Hz), 7.17 (s, 1H), 7.15 (s, 1H), 5.34–5.25 (m, 1H), 4.45–4.40 (br.-d, 2H), 4.22 (q, 2H, J=7.0 Hz), 4.17 (q, 2H, J=7.0 Hz), 3.60 (s, 3H), 3.25–3.16 (br.-t, 2H), 3.10–3.00 (m, 2H), 1.89–1.84 (br.-d, 2H), 1.53 (t, 3H, J=7.0 Hz), 1.52 (t, 3H, J=7.0 Hz).

IR (KBr tab.)(cm⁻¹): 1704, 1657, 1508, 1148, 754.

Melting Point (ethyl acetate-ether): 191–193° C.

REFERENCE EXAMPLE 17

3-[1-(2-Chloro-6,7-diethoxy-4-quinazolinyl)-4-piperidinyl]-1,2,3,4-tetrahydro-6-methyl-2,4-dioxoquinazoline (Compound r)

¹H-NMR (CDCl₃) δ: 9.39 (br.-s, 1H, NH), 7.92 (d, 1H, J=2.0 Hz), 7.42 (dd, 1H, J=8.0, 2.0 Hz), 7.17 (s, 1H), 7.15 (s, 1H), 6.93 (d, 1H, J=8.0 Hz), 5.26–5.10 (m, 1H), 4.47–4.42 (br.-d, 2H), 4.22 (q, 2H, J=7.0 Hz), 4.17 (q, 2H, J=7.0 Hz), 3.29–3.20 (br.-t, 2H), 3.09–2.97 (m, 2H), 2.41 (s, 3H), 1.89–1.85 (br.-d, 2H), 1.53 (t, 3H, J=7.0 Hz), 1.51 (t, 3H, J=7.0 Hz).

IR (KBr tab.)(cm⁻¹): 1705, 1655, 1560, 1458.

Melting Point (ethyl acetate-ether): 187–190° C.

REFERENCE EXAMPLE 18

3-[1-(2-Chloro-6,7-diethoxy-4-quinazolinyl)-4-piperidinyl]-1-ethyl-1,2,3,4-tetrahydro-6-methyl-2,4-dioxoquinazoline (Compound s)

¹-NMR (CDCl₃) δ: 8.02 (d, 1H, J=2.0 Hz), 7.47 (dd, 1H, J=8.6, 2.0 Hz), 7.15 (s, 2H), 7.10 (d, 1H, J=8.6 Hz), 5.32–5.24 (m, 1H), 4.44–4.40 (br.-d, 2H), 4.21 (q, 2H, J=7.0 Hz), 4.17 (q, 2H, J=7.0 Hz), 4.16 (q, 2H, J=7.0 Hz), 3.25–3.16 (br.-t, 2H), 3.10–2.97 (m, 2H), 2.41 (s, 3H), 1.88–1.83 (br.-d, 2H), 1.53 (t, 3H, J=7.0 Hz), 1.52 (t, 3H, J=7.0 Hz), 1.35 (t, 3H, J=7.0 Hz).

IR (KBr tab.)(cm$^{-1}$): 1702, 1655, 1526, 1459.

Melting Point (methanol-water): 202–203° C.

REFERENCE EXAMPLE 19

3-[1-(2-Chloro-6,7-diethoxy-4-quinazolinyl)-4-piperidinyl]-1,2,3,4-tetrahydro-6-methyl-2,4-dioxo-1-propylquinazoline (Compound t)

$^1$H-NMR (CDCl$_3$) δ: 8.02 (d, 1H, J=2.0 Hz), 7.47 (dd, 1H, J=8.3, 2.0 Hz), 7.15 (s, 2H), 7.07 (d, 1H, J=8.3 Hz), 5.33–5.24 (m, 1H), 4.45–4.40 (br.-d, 2H), 4.22 (q, 2H, J=7.0 Hz), 4.17 (q, 2H, J=7.0 Hz), 4.08–4.02 (br.-t, 2H), 3.25–3.16 (br.-t, 2H), 3.09–2.97 (m, 2H), 2.41 (s, 3H), 1.88–1.83 (br.-d, 2H), 1.81–1.72 (m, 2H), 1.53 (t, 3H, J=7.0 Hz), 1.52 (t, 3H, J=7.0 Hz), 1.04 (t, 3H, J=7.0 Hz).

IR (KBr tab.)(cm$^{-1}$): 1699, 1655, 1511, 1507, 1249.

Melting Point (ether): 227–230° C.

REFERENCE EXAMPLE 20

3-[1-(2-Chloro-6,7-diethoxy-4-quinazolinyl)-4-piperidinyl]-1,2,3,4-tetrahydro-5-methyl-2,4-dioxoquinazoline (Compound u)

$^1$H-NMR (CDCl$_3$) δ: 9.22 (br.-s, 1H, NH), 7.44 (dd, 1H, J=7.5, 7.5 Hz), 7.18 (s, 1H), 7.15 (s, 1H), 7.00 (d, 1H, J=7.5 Hz), 6.85 (d, 1H, J=7.5 Hz), 5.28–5.18 (m, 1H), 4.48–4.43 (br.-d, 2H), 4.24 (q, 2H, J=7.0 Hz), 4.16 (q, 2H, J=7.0 Hz), 3.28–3.18 (br.-t, 2H), 3.10–2.94 (m, 2H), 2.79 (s, 3H), 1.88–1.84 (br.-d, 2H), 1.54 (t, 3H, J=7.0 Hz), 1.52 (t, 3H, J=7.0 Hz).

IR (KBr tab.)(cm$^{-1}$): 1717, 1654, 1252, 794.

Melting Point (methanol-water): 259–261° C.

REFERENCE EXAMPLE 21

3-[1-(2-Chloro-6,7-diethoxy-4-quinazolinyl)-4-piperidinyl]-1,2,3,4-tetrahydro-1,5-dimethyl-2,4-dioxoquinazoline (Compound v)

$^1$H-NMR (CDCl$_3$) δ: 7.51 (dd, 1H, J=7.6, 7.6 Hz), 7.16 (s, 2H), 7.07 (d, 2H, J=7.6 Hz), 5.31–5.22 (m, 1H), 4.46–4.41 (br.-d, 2H), 4.20 (q, 2H, J=7.0 Hz), 4.17 (q, 2H, J=7.0 Hz), 3.58 (s, 3H), 3.25–3.16 (br.-t, 2H), 3.05–2.99 (m, 2H), 2.82 (s, 3H), 1.88–1.83 (br.-d, 2H), 1.53 (t, 3H, J=7.0 Hz), 1.52 (t, 3H, J=7.0 Hz).

IR (KBr tab.)(cm$^{-1}$): 1704, 1698, 1659, 1649, 1573, 1475, 755.

Melting Point (methanol-water): 199–201° C.

REFERENCE EXAMPLE 22

3-[1-(2-Chloro-6,7-diethoxy-4-quinazolinyl)-4-piperidinyl]-1,2,3,4-tetrahydro-8-methyl-2,4-dioxoquinazoline (Compound w)

$^1$H-NMR (CDCl$_3$) δ: 8.63 (br.-s, 1H, NH), 8.01 (d, 1H, J=8.0 Hz), 7.43 (d, 1H, J=8.0 Hz), 7.19 (s, 1H), 7.14 (dd, 2H, J=8.0, 8.0 Hz), 7.14 (s, 1H), 5.30–5.20 (m, 1H), 4.48–4.43 (br.-d, 2H), 4.23 (q, 2H, J=7.0 Hz), 4.16 (q, 2H, J=7.0 Hz), 3.25–3.21 (br.-t, 2H), 3.07–2.99 (m, 2H), 2.35 (s, 3H), 1.89–1.85 (br.-d, 2H), 1.53 (t, 3H, J=7.0 Hz), 1.51 (t, 3H, J=7.0 Hz).

IR (KBr tab.)(cm$^{-1}$): 1707, 1656, 1650, 755.

Melting Point (methanol-water): 246–248° C.

REFERENCE EXAMPLE 23

3-[1-(2-Chloro-6,7-diethoxy-4-quinazolinyl)-4-piperidinyl]-1,2,3,4-tetrahydro-1,8-dimethyl-2,4-dioxoquinazoline (Compound x)

$^1$H-NMR (CDCl$_3$) δ: 8.06 (d, 1H, J=7.0 Hz), 7.46 (d, 1H, J=7.0 Hz), 7.17 (dd, 1H, J=7.0, 7.0 Hz), 7.15 (s, 1H), 7.14 (s, 1H), 5.20–5.05 (m, 1H), 4.43–4.39 (br.-d, 2H), 4.22 (q, 2H, J=7.0 Hz), 4.18 (q, 2H, J=7.0 Hz), 3.67 (s, 3H), 3.24–2.99 (m, 4H), 2.61 (s, 3H), 1.89–1.85 (br.-d, 2H), 1.53 (t, 3H, J=7.0 Hz), 1.52 (t, 3H, J=7.0 Hz).

IR (KBr tab.)(cm$^{-1}$): 1726, 1674, 1514, 1269.

Melting Point (methanol-water): 206–207° C.

REFERENCE EXAMPLE 24

6-Chloro-3-[1-(2-chloro-6,7-diethoxy-4-quinazolinyl)-4-piperidinyl]-1,2,3,4-tetrahydro-2,4-dioxoquinazoline (Compound y)

$^1$H-NMR (CDCl$_3$) δ: 9.50 (br.-s, 1H, NH), 7.92 (d, 1H, J=2.0 Hz), 7.43 (dd, 1H, J=8.5, 2.0 Hz), 7.19 (s, 1H), 7.15 (s, 1H), 6.94 (d, 1H, J=8.0 Hz), 5.31–5.23 (m, 1H), 4.48–4.43 (br.-d, 2H), 4.23 (q, 2H, J=7.0 Hz), 4.16 (q, 2H, J=7.0 Hz), 3.29–3.20 (br.-t, 2H), 3.09–2.97 (m, 2H), 1.89–1.85 (br.-d, 2H), 1.53 (t, 3H, J=7.0 Hz), 1.50 (t, 3H, J=7.0 Hz).

IR (KBr tab.)(cm$^{-1}$): 1709, 1667, 1431, 1247.

Melting Point (ether): 236–239° C.

REFERENCE EXAMPLE 25

6-Chloro-3-[1-(2-chloro-6,7-diethoxy-4-quinazolinyl)-4-piperidinyl]-1,2,3,4-tetrahydro-1-methyl-2,4-dioxoquinazoline (Compound z)

$^1$H-NMR (CDCl$_3$) δ: 8.18 (d, 1H, J=2.5 Hz), 7.62 (dd, 1H, J=8.9, 2.5 Hz), 7.16 (s, 1H), 7.14 (s, 1H), 7.14 (d, 1H, J=8.9 Hz), 5.40–5.20 (m, 1H), 4.44–4.39 (br.-d, 2H), 4.22 (q, 2H, J=7.0 Hz), 4.17 (q, 2H, J=7.0 Hz), 3.58 (s, 3H), 3.25–3.16 (br.-t, 2H), 3.02–2.96 (m, 2H), 1.87–1.83 (br.-d, 2H), 1.53 (t, 3H, J=7.0 Hz), 1.52 (t, 3H, J=7.0 Hz).

IR (KBr tab.)(cm$^{-1}$): 1705, 1659, 1573, 1511, 1493, 754.

Melting Point (methanol-water): 227–228° C.

REFERENCE EXAMPLE 26

6-Bromo-3-[1-(2-chloro-6,7-diethoxy-4-quinazolinyl)-4-piperidinyl]-1,2,3,4-tetrahydro-1-methyl-2,4-dioxoquinazoline (Compound aa)

$^1$H-NMR (CDCl$_3$) δ: 8.33 (d, 1H, J=2.6 Hz), 7.76 (dd, 1H, J=8.9, 2.6 Hz), 7.18 (s, 1H), 7.14 (s, 1H), 7.08 (d, 1H, J=8.9 Hz), 5.30–5.20 (m, 1H), 4.45–4.40 (br.-d, 2H), 4.22 (q, 2H, J=7.0 Hz), 4.17 (q, 2H, J=7.0 Hz), 3.58 (s, 3H), 3.25–3.16 (br.-t, 2H), 3.06–2.93 (m, 2H), 1.86–1.82 (br.-d, 2H), 1.53 (t, 3H, J=7.0 Hz), 1.52 (t, 3H, J=7.0 Hz).

IR (KBr tab.)(cm$^{-1}$): 1727, 1683, 1594, 1514, 1270.

Melting Point (methanol-water): 247–248° C.

REFERENCE EXAMPLE 27

3-[1-(2-Chloro-6,7-diethoxy-4-quinazolinyl)-4-piperidinyl]-1,2,3,4-tetrahydro-6-nitro-2,4-dioxoquinazoline (Compound bb)

$^1$H-NMR (CDCl$_3$) δ: 11.86 (br.-s, 1H, NH), 8.92 (d, 1H, J=2.0 Hz), 8.36 (dd, 1H, J=8.5, 2.0 Hz), 7.31 (d, 1H, J=8.5

Hz), 7.19 (s, 1H), 7.15 (s, 1H), 5.30–5.20 (m, 1H), 4.51–4.46 (br.-d, 2H), 4.23 (q, 2H, J=7.0 Hz), 4.18 (q, 2H, J=7.0 Hz), 3.30–3.21 (br.-t, 2H), 3.04–2.95 (m, 2H), 1.90–1.85 (br.-d, 2H), 1.53 (t, 3H, J=7.0 Hz), 1.53 (t, 3H, J=7.0 Hz).

IR (KBr tab.)(cm$^{-1}$): 1721, 1691, 1675, 1334.

Melting Point (ether): 177–180° C.

REFERENCE EXAMPLE 28

3-[1-(2-Chloro-6,7-diethoxy-4-quinazolinyl)-4-piperidinyl]-1,2,3,4-tetrahydro-1-methyl-6-nitro-2,4-dioxoquinazoline (Compound cc)

$^1$H-NMR (CDCl$_3$) δ: 9.08 (d, 1H, J=2.6 Hz), 8.51 (dd, 1H, J=9.0, 2.6 Hz), 7.32 (d, 1H, J=9.0 Hz), 7.17 (s, 1H), 7.14 (s, 1H), 5.31–5.23 (m, 1H), 4.46–4.41 (br.-d, 2H), 4.22 (q, 2H, J=7.0 Hz), 4.18 (q, 2H, J=7.0 Hz), 3.67 (s, 3H), 3.27–3.18 (br.-t, 2H), 3.06–2.92 (m, 2H), 1.88–1.85 (br.-d, 2H), 1.53 (t, 3H, J=7.0 Hz), 1.53 (t, 3H, J=7.0 Hz).

IR (KBr tab.)(cm$^{-1}$): 1710, 1665, 1616, 1334, 1230, 1025.

Melting Point (methanol-water): 239–241° C.

REFERENCE EXAMPLE 29

6-Acetyl-3-[1-(2-chloro-6,7-diethoxy-4-quinazolinyl)-4-piperidinyl]-1,2,3,4-tetrahydro-1-methyl-2,4-dioxoquinazoline (Compound dd)

$^1$H-NMR (CDCl$_3$) δ: 8.76 (d, 1H, J=2.0 Hz), 8.31 (dd, 1H, J=8.9, 2.0 Hz), 7.29 (d, 1H, J=8.9 Hz), 7.17 (s, 1H), 7.15 (s, 1H), 5.30–5.10 (m, 1H), 4.45–4.41 (br.-d, 2H), 4.22 (q, 2H, J=7.0 Hz), 4.18 (q, 2H, J=7.0 Hz), 3.64 (s, 3H), 3.27–3.18 (br.-t, 2H), 3.07–3.00 (m, 2H), 2.67 (s, 3H), 1.89–1.85 (br.-d, 2H), 1.53 (t, 6H, J=7.0 Hz).

IR (KBr tab.)(cm$^{-1}$): 1708, 1685, 1655, 1615, 1543, 1512, 1235.

Melting point (methanol-water): 204–206° C.

What is claimed is:

1. A quinazoline derivative represented by formula (I):

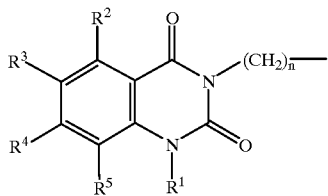

(I)

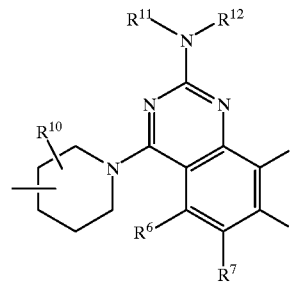

wherein $R^1$ represents hydrogen, lower alkyl (said lower alkyl being optionally substituted with 1 to 3 substituents independently selected from the group consisting of halogen, nitro, cyano, hydroxy, lower alkoxy, carboxy, lower alkoxycarbonyl, lower alkanoyl, cycloalkyl, amino, mono- or di(lower alkyl)amino, phthalimido or CONR$^{13}$R$^{14}$ (wherein R$^{13}$ and R$^{14}$ independently represent hydrogen, lower alkyl, or R$^{13}$ and R$^{14}$ are combined together with N to form a heterocycle selected from the group consisting of pyrrolidinyl, piperidino, piperazinyl, morpholino, thiomorpholino, homopiperazinyl and homopiperidino)), alkenyl or C$_{7-13}$ aralkyl (said aralkyl being optionally substituted on the benzene ring thereof with 1 to 3 substituents independently selected from the group consisting of halogen, lower alkyl, nitro, cyano, amino, mono- or di(lower alkyl)amino, hydroxy lower alkoxy, carboxy, lower alkoxycarbonyl, lower alkanoyl, methylenedioxy and trifluoromethyl);

$R^2$, $R^3$, $R^4$ and $R^5$ independently represent hydrogen, halogen, amino, mono- or di(lower alkyl)amino, lower alkanoylamino, nitro, cyano, lower alkyl (said lower alkyl being optionally substituted with 1 to 3 substituents independently selected from the group consisting of halogen, nitro, cyano, hydroxy, lower alkoxy, carboxy, lower alkoxycarbonyl, lower alkanoyl, cycloalkyl, amino, mono- or di(lower alkyl)amino, phthalimido or CONR$^{13}$R$^{14}$ (wherein R$^{13}$ and R$^{14}$ independently represent hydrogen, lower alkyl, or R$^{13}$ and R$^{14}$ are combined together with N to form a heterocycle selected from the group consisting of pyrrolidinyl, piperidino, piperazinyl morpholino, thiomorpholino, homopiperazinyl and homopiperidino)), hydroxy, lower alkoxy, lower alkylthio, carboxy, lower alkoxycarbonyl, lower alkanoyl, aralkyloxy having a C$_{7-13}$ aralkyl moiety or lower alkanoyloxy;

$R^6$, $R^7$, $R^8$ and $R^9$ independently represent hydrogen, lower alkyl, hydroxy, lower alkoxy (said lower alkoxy being optionally substituted with 1 to 3 substituents independently selected from the group consisting of halogen, nitro, cyano, hydroxy, lower alkoxy, carboxy, lower alkoxycarbonyl, lower alkanoyl, cycloalkyl, amino, mono- or di(lower alkyl)amino, phthalimido or CONR$^{13}$R$^{14}$ (wherein R$^{13}$ and R$^{14}$ independently represent hydrogen, lower alkyl, or R$^{13}$ and R$^{14}$ are combined together with N to form a heterocycle selected from the group consisting of pyrrolidinyl, piperidino, piperazinyl, morpholino, thiomorpholino, homopiperazinyl and homopiperidino)), aralkyloxy having a C$_{7-13}$ aralkyl moiety, or lower alkanoyloxy, or any adjoining two of them are combined to form methylenedioxy or ethylenedioxy;

$R^{10}$ represents hydrogen, lower alkyl, or halogen;

$R^{11}$ and $R^{12}$ independently represent hydrogen, lower alkyl (said lower alkyl being optionally substituted with 1 to 3 substituents independently selected from the group consisting of halogen, nitro, cyano, hydroxy, lower alkoxy, carboxy, lower alkoxycarbonyl, lower alkanoyl, cycloalkyl, amino. mono- or di(lower alkyl) amino, phthalimido or CONR$^{13}$R$^{14}$ (wherein R$^{13}$ and R$^{14}$ independently represent hydrogen, lower alkyl, or R$^{13}$ and R$^{14}$ are combined together with N to form a heterocycle selected from the group consisting of pyrrolidinyl, piperidino, piperazinyl, morpholino, thiomorpholino, homopiperazinyl and homopineridino)), cycloalkyl, phenyl (said phenyl being optionally substituted on the benzene ring thereof with 1 to 3 substituents independently selected from the group consisting of halogen, lower alkyl, nitro, cyano, amino, mono- or di(lower alkyl)amino, hydroxy, lower alkoxy, carboxy, lower alkoxycarbonyl, lower alkanoyl, methylenedioxy and trifluoromethyl) or C$_{7-13}$ aralkyl (said aralkyl being optionally substituted on the benzene ring thereof with 1 to 3 substituents independently selected from the group consisting of halogen, lower alkyl, nitro, cyano, amino, mono- or di(lower alkyl)amino, hydroxy, lower alkoxy, carboxy, lower alkoxycarbonyl, lower alkanoyl, methylenedioxy and trifluoromethyl), or $R^{11}$ and $R^{12}$ are combined together with N to form a heterocycle selected from the group consisting of pyrrolidinyl, piperidino, piperazinyl, morpholino, thiomorpholino, homopiperazinyl and homopiperidino (said heterocycle being optionally substituted with 1 to 3 substituents independently selected from the group consisting of halogen, lower alkyl, amino, mono- or di(lower alkyl)amino, hydroxy, lower alkoxy, carboxy, lower alkoxycarbonyl, lower alkanoyl, trifluoromethyl, phenyl and $C_{7-13}$ aralkyl); and n represents 0, 1 or 2, or a pharmaceutically acceptable salt thereof.

2. A compound according to claim 1 wherein $R^1$ represents hydrogen or lower alkyl.

3. A compound according to claim 1 wherein $R^2$, $R^3$, $R^4$, and $R^5$ independently represent hydrogen, halogen, nitro, lower alkyl, or lower alkanoyl.

4. A compound according to claim 1 wherein $R^6$, $R^7$, $R^8$, and $R^9$ independently represent hydrogen or lower alkoxy, or any adjoining two of them are combined to form methylenedioxy.

5. A compound according to claim 1 wherein $R^{11}$ and $R^{12}$ independent represent hydrogen, said optionally substituted lower alkyl or $C_{7-13}$ aralkyl, or $R^{11}$ and $R^{12}$ are combined together with N to form said optionally substituted heterocycle.

6. A compound according to claim 1 wherein n represents 0.

7. A compound according to claim 5 wherein said heterocyclic group formed by $R^{11}$ and $R^{12}$ combined together with N is morpholino.

8. A pharmaceutical composition comprising a compound according to claim 1 and a pharmaceutically acceptable carrier.

9. A therapeutical agent for treating nephritis or diabetic nephropathy which comprises a compound according to claim 1 and a pharmaceutically acceptable carrier.

10. A method of treating nephritis or diabetic nephropathy which comprises administering an effective amount of a compound according to claim 1.

* * * * *

UNITED STATES PATENT AND TRADEMARK OFFICE
CERTIFICATE OF CORRECTION

PATENT NO. : 5,948,784
DATED : September 7, 1999
INVENTOR(S) : Shigeki Fujiwara

It is certified that error appears in the above-identified patent and that said Letters Patent is hereby corrected as shown below:

ON THE TITLE PAGE [56] References Cited:

FOREIGN PATENT DOCUMENTS, after "Hess et al.," "91968)" should read --(1968)--.

ON THE TITLE PAGE [75]:

Inventors, "Haruki Takai, Shizuoka;" should read --Haruku Taki, Yokohama;-- and "Takahiro Moriyama, Shizuoka;" should read --Takahiro Moriyama, Ichikawa;--.

COLUMN 5:

Line 1, "Hydolysis" should read --Hydrolysis--.

COLUMN 13:

Line 22, "carrired" should read --carried--.

UNITED STATES PATENT AND TRADEMARK OFFICE
CERTIFICATE OF CORRECTION

PATENT NO. : 5,948,784

DATED : September 7, 1999

INVENTOR(S) : Shigeki Fujiwara

It is certified that error appears in the above-identified patent and that said Letters Patent is hereby corrected as shown below:

COLUMN 21:

Table 7,

"administered group"

should read

-- administered group --.

**: The data differed significantly from that on the control group at the less than 1% level.

COLUMN 28:

Line 11, "35 6.90" should read --6.90--.

COLUMN 37:

Line 38, "dropwised" should read --added dropwise--.

COLUMN 40:

Line 45, "mixtute" should read --mixture--.

UNITED STATES PATENT AND TRADEMARK OFFICE
CERTIFICATE OF CORRECTION

PATENT NO.  : 5,948,784
DATED       : September 7, 1999
INVENTOR(S) : Shigeki Fujiwara It is certified that error appears in the above-identified patent and that said Letters Patent is hereby corrected as shown below:

COLUMN 41:

Line 1, "dropwised" should read --added dropwise--;
    Line 7, "was dropwised" should read --were added dropwise--; and
    Line 6, "tirethylamine" should read --triethylamine--.

COLUMN 42:

Line 17, "(2-hydrorxyethyl)oxy-2-" should read --(2-hydroxyethyl)oxy-2- --.

COLUMN 54:

Line 6 "independent" should read --independently--.

Signed and Sealed this

Eighteenth Day of July, 2000

Q. TODD DICKINSON

*Attest:*

*Attesting Officer*      *Director of Patents and Trademarks*